United States Patent [19]
Johnson et al.

[11] Patent Number: 5,817,052
[45] Date of Patent: Oct. 6, 1998

[54] APPARATUS FOR INTRAOSSEOUS INFUSION OR ASPIRATION

[75] Inventors: David L. Johnson; Judith M. Findlay, both of Burnaby; David Higgs; William Eric McMorran, both of Vancouver; Michael W. Jacobs, Surrey, all of Canada

[73] Assignee: Pyng Medical Corp., Vancouver, Canada

[21] Appl. No.: 578,042

[22] Filed: Dec. 26, 1995

[51] Int. Cl.⁶ .................................................. A61M 31/00
[52] U.S. Cl. .............................. 604/51; 604/264; 128/751
[58] Field of Search .................................. 604/51, 49, 27, 604/28, 264, 19, 21; 128/751, 753, 754

[56] References Cited

U.S. PATENT DOCUMENTS

| | | |
|---|---|---|
| 1,523,068 | 1/1925 | Hein . |
| 2,426,535 | 8/1947 | Turkel . |
| 2,705,949 | 4/1955 | Silverman . |
| 2,773,500 | 12/1956 | Young . |
| 2,773,501 | 12/1956 | Young . |
| 3,310,051 | 3/1967 | Schulte . |
| 3,750,667 | 8/1973 | Pshenichny et al. . |
| 3,783,876 | 1/1974 | Dye . |
| 3,815,605 | 6/1974 | Schmidt et al. . |
| 4,170,993 | 10/1979 | Alvarez . |
| 4,469,109 | 9/1984 | Mehl . |
| 4,496,342 | 1/1985 | Banko . |
| 4,710,171 | 12/1987 | Rosenberg . |
| 4,743,231 | 5/1988 | Kay et al. . |
| 4,747,414 | 5/1988 | Brossel . |
| 4,763,667 | 8/1988 | Manzo . |
| 4,772,261 | 9/1988 | Von Hoff et al. . |
| 4,969,870 | 11/1990 | Kramer et al. . |
| 5,176,643 | 1/1993 | Kramer et al. . |
| 5,176,662 | 1/1993 | Bartholomew et al. . |
| 5,271,744 | 12/1993 | Kramer et al. . |
| 5,312,364 | 5/1994 | Jacobs . |
| 5,332,398 | 7/1994 | Miller et al. . |
| 5,372,583 | 12/1994 | Roberts et al. . |
| 5,431,655 | 7/1995 | Melker et al. . |

FOREIGN PATENT DOCUMENTS

| | | |
|---|---|---|
| 1315796 | 5/1973 | United Kingdom . |

OTHER PUBLICATIONS

Clinical Procedures in Emergency Medicine, 2nd ed., Roberts Hedges, 1991, Chapter 29, "Intraosseous Infusion" by William H. Spivey.

T. Sugihara, et al., The extensibility in human skin: variation according to age and site, British Journal of Plastic Surgery (1991), 44, 418–422.

(List continued on next page.)

*Primary Examiner*—John D. Yasko
*Attorney, Agent, or Firm*—Oyen Wiggs Green & Mutala

[57] ABSTRACT

An apparatus comprising three main assemblies, an applicator, an infusion/aspiration tube with a subcutaneous bone penetration means, and a strain relief protector. The apparatus enables a user in field or emergency environments to quickly, safely and reliably place an infusion/aspiration device in a patient's bone, regardless of the thickness of skin and tissue over the bone, and to ensure it will remain in place throughout other emergency procedures and severe environmental conditions. The infusion/aspiration apparatus incorporates a bone stop to ensure precise location of the bone penetration means at the intended marrow depth in the patient's bone. A method of intraosseous infusion or aspiration has a first step of locating the appropriate site on a suitable bone, a second step of inserting a bone penetration means device through the skin using an applicator, a third step of placing a fluid delivery port at a precise depth by mechanical location means which use the surface of the target bone as a reference point, a fourth step of removing the applicator, an optional fifth step of installing a strain relief protector, and a final step of attaching a source of fluids for infusion or of suction for aspiration.

27 Claims, 12 Drawing Sheets

OTHER PUBLICATIONS

L.M. Tocantins and J.F. O'Neill, Infusion of Blood and Other Fluids into the Circulation via the Bone Marrow.

Perry M. Shoor, et al., Intraosseous Infusion: Pressure–flow Relationship and Pharmacokinetics, The Journal of Trauma, 1979, vol. 19, No. 10, pp. 772–774.

Valerie A. Rosetti, et al., Intraosseous Infusion: An Alternative Route of Pediatric Intravascular Access, Annals of Emergency Medicine, 14:9 Sep. 1985, pp. 103–106.

William H. Spivey, Medical Progress, Journal of Pediatrics, Nov. 1987, vol. 3, No. 5, pp. 639–643.

James P. Orlowski, et al., Comparison Study of Intraosseous, Central Intravenous, and Peripheral Intravenous Infusions of Emergency Drugs, AJDC–vol. 144, Jan. 1990, pp. 112–117.

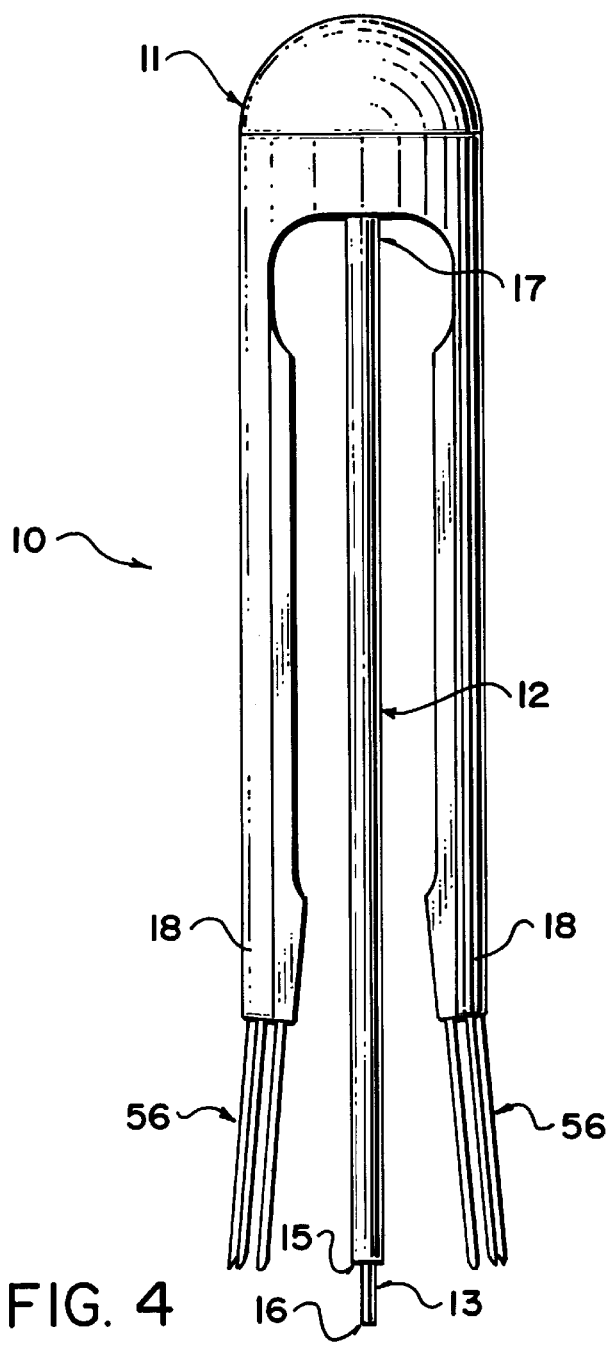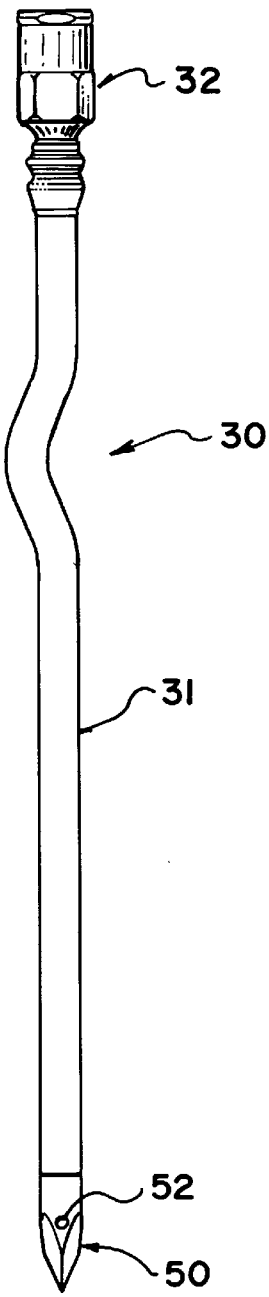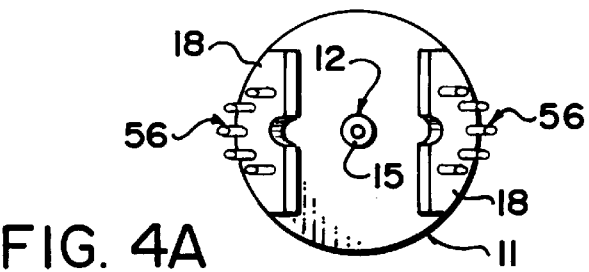
FIG. 4
FIG. 4A
FIG. 5

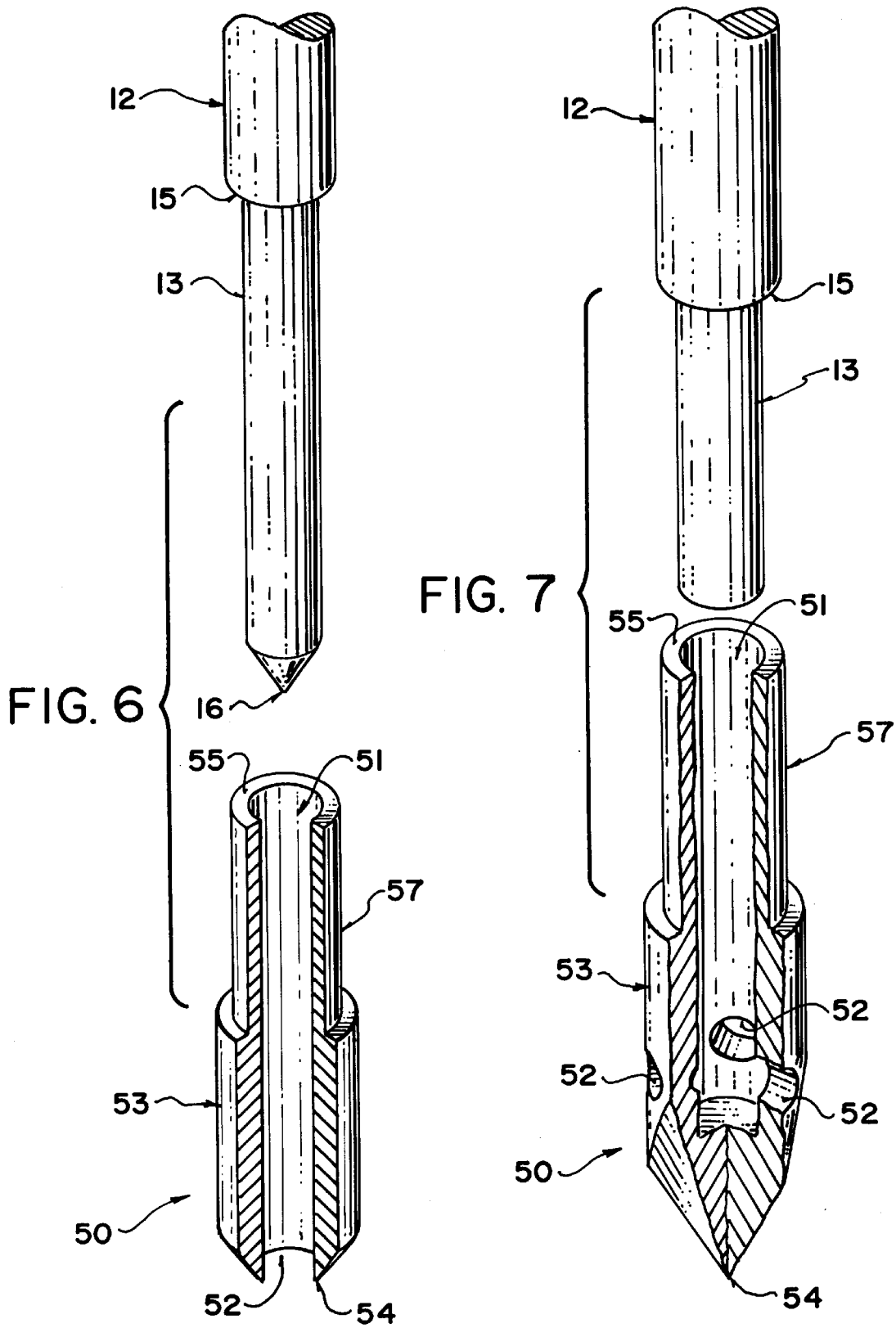

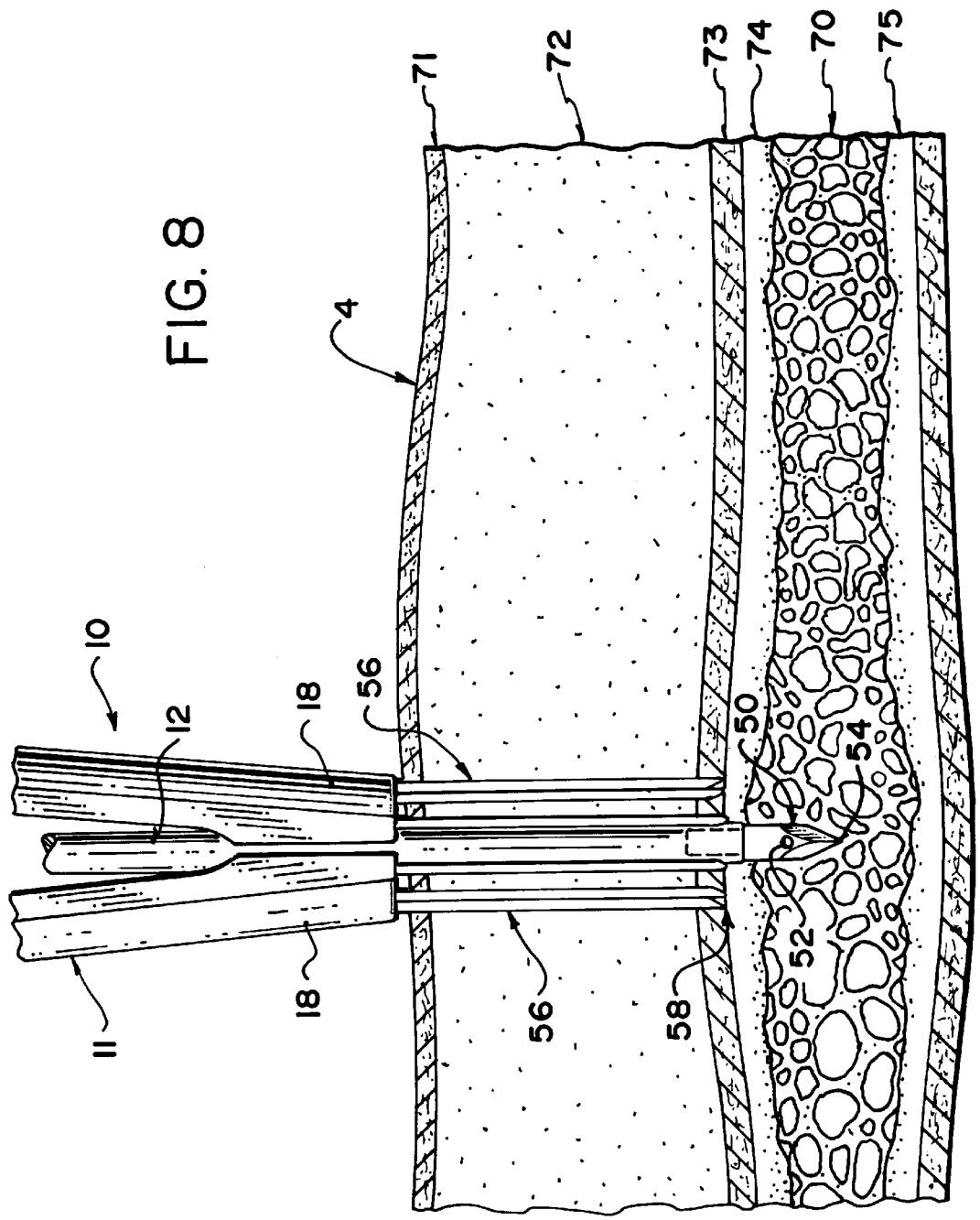

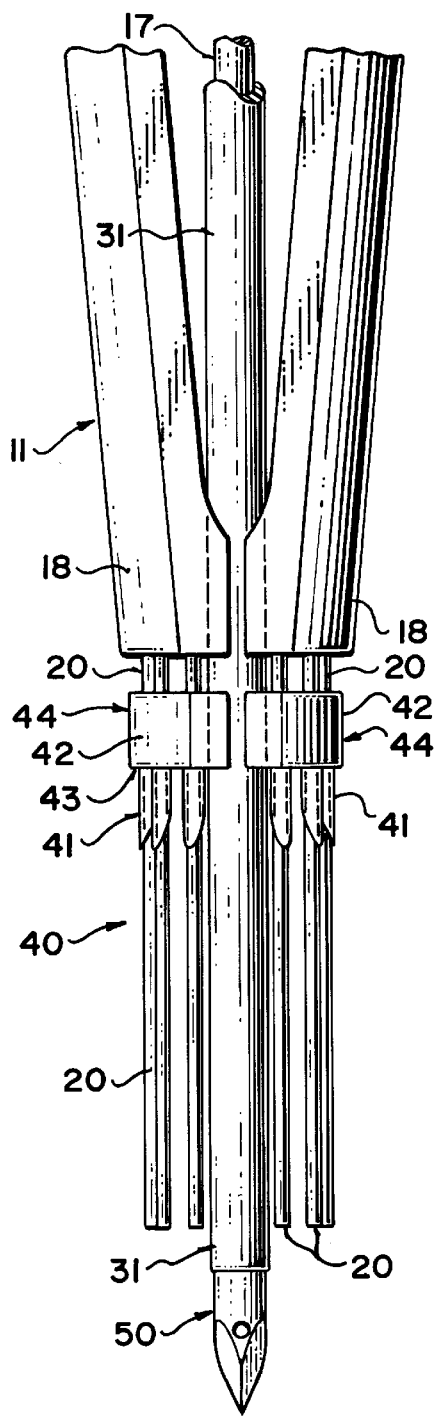
FIG. 13
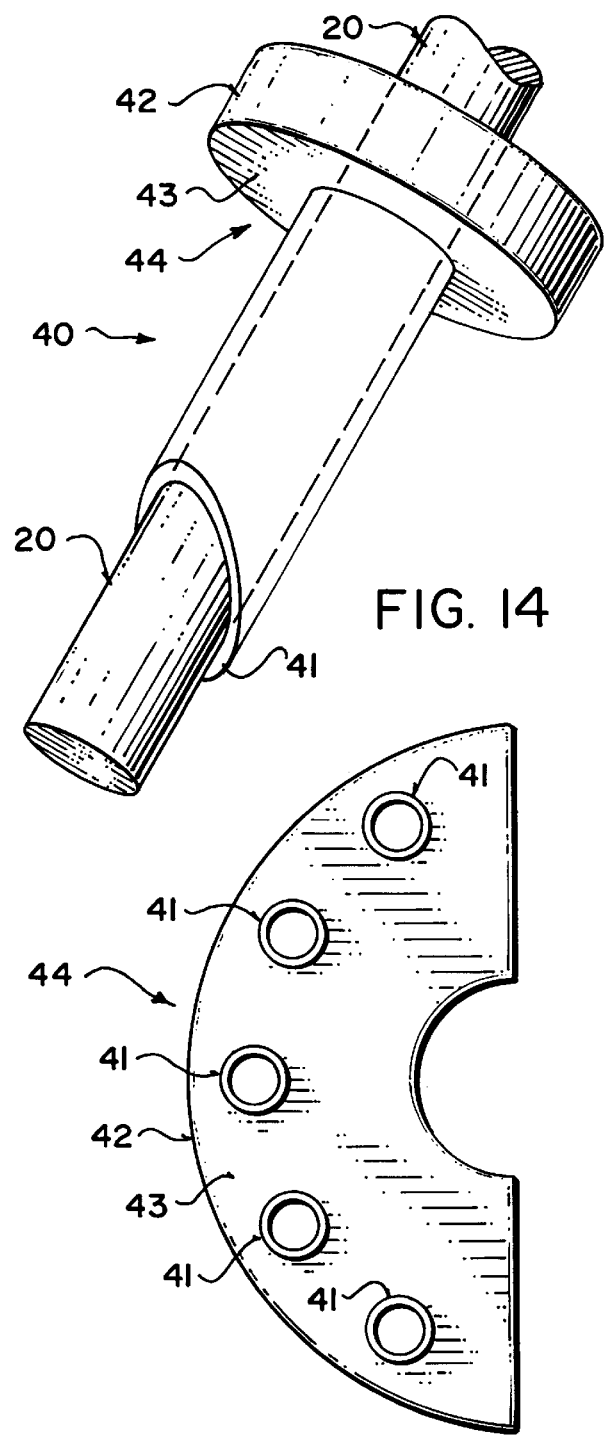
FIG. 14
FIG. 17

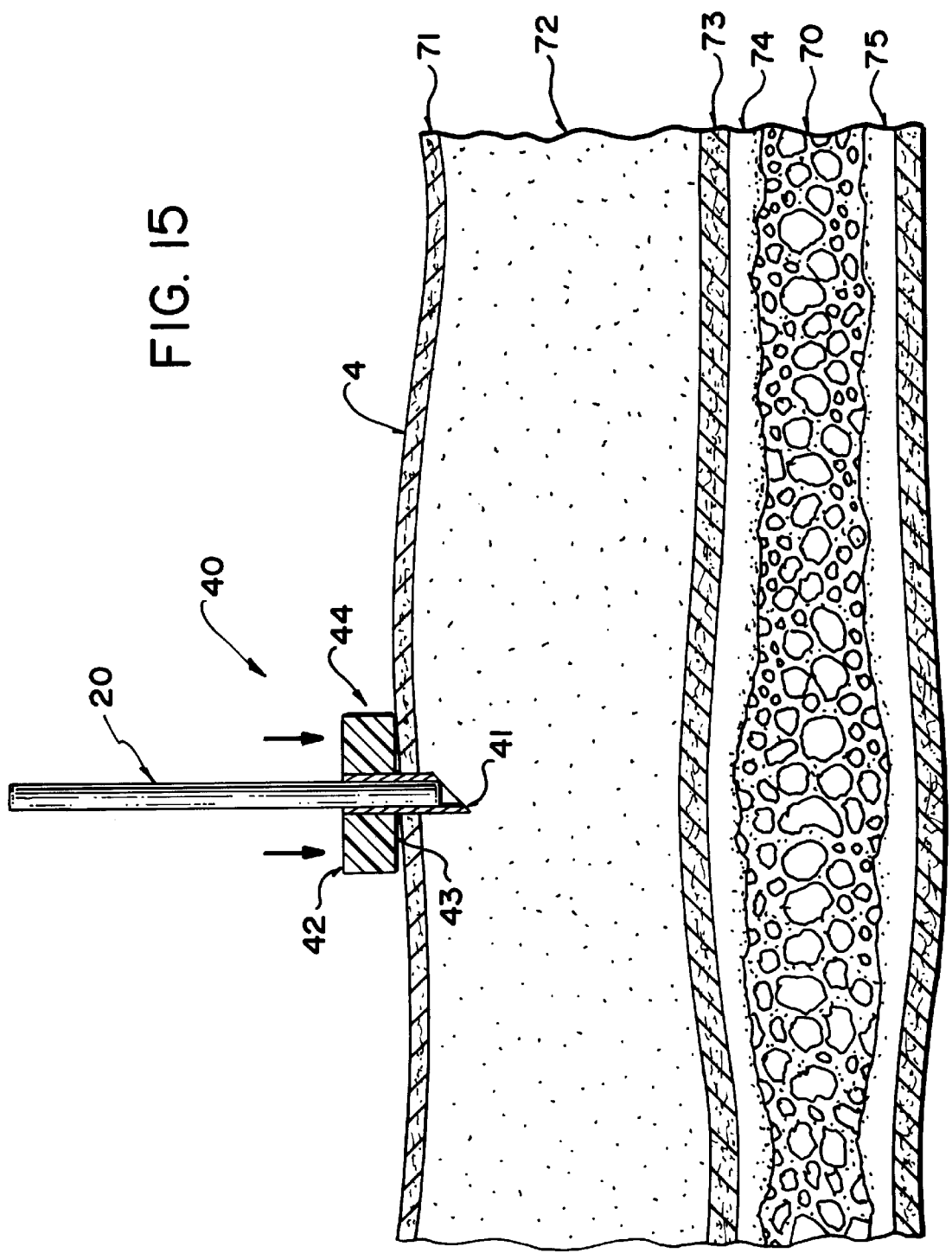

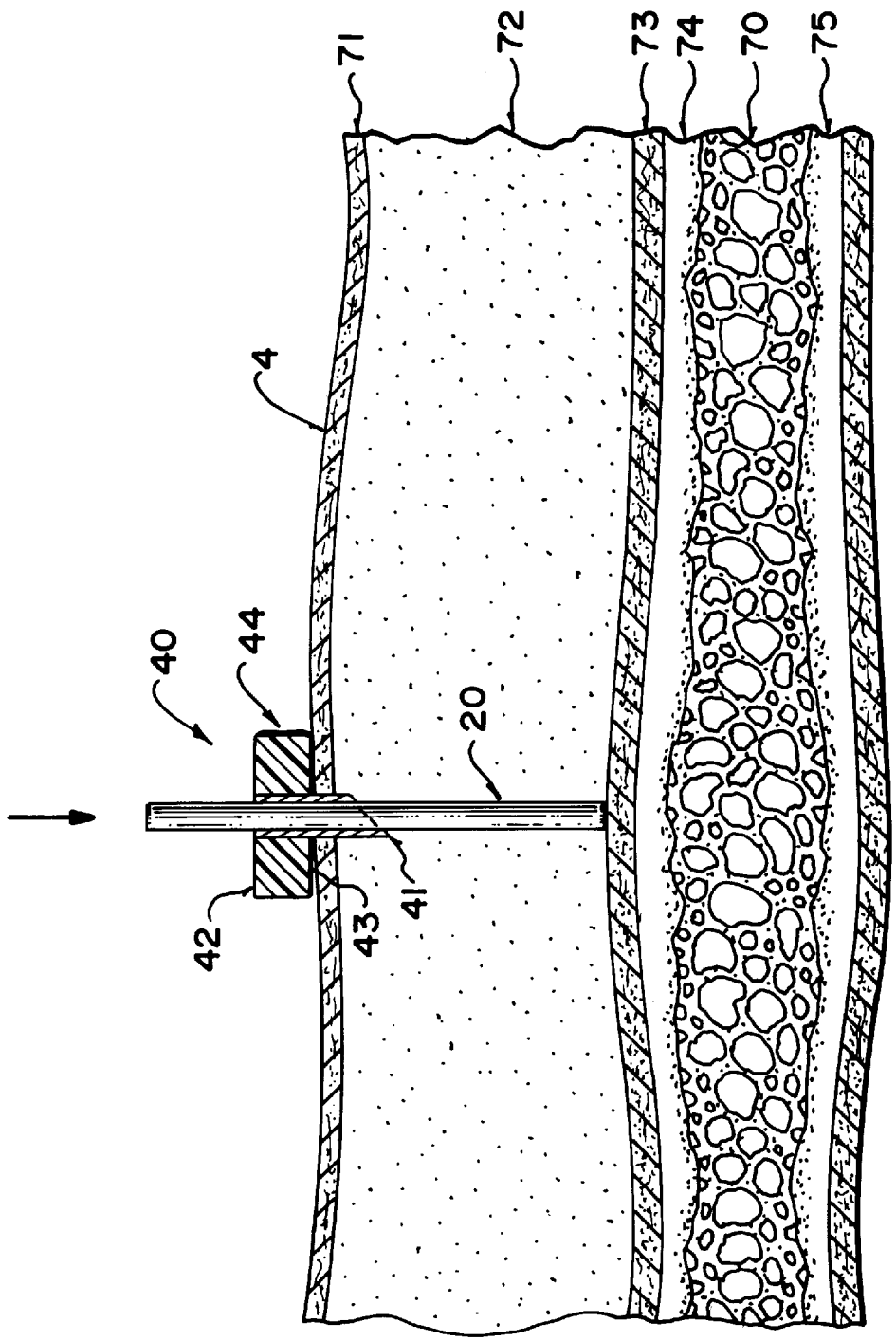

APPARATUS FOR INTRAOSSEOUS INFUSION OR ASPIRATION

FIELD OF THE INVENTION

This invention relates to novel methods and apparatus for infusing liquids into bone marrow under field and emergency conditions, or aspirating bone marrow. More particularly, the invention pertains to novel methods and apparatus in which liquids are infused at a precisely controlled depth in the bone marrow, thereby ensuring proper infusion and minimizing risk.

BACKGROUND OF THE INVENTION

Drugs and other liquids are customarily delivered to patients via their vascular systems, using a needle or catheter inserted into a peripheral blood vessel. This process is called intravenous (IV) infusion. The IV technique for vascular access functions generally satisfactorily in cases where the patient's blood pressure is at normal levels. However, in cases where the patient is in circulatory shock due to heart failure, drug overdose, or severe hemorrhaging, the peripheral blood vessels frequently are collapsed and access to those blood vessels can be difficult. Peripheral vessel catheterization also is exceedingly difficult in pediatric patients because of the small size of their peripheral vessels.

When vascular access must be achieved rapidly under emergency, battlefield, or first response conditions, the difficulty of successfully achieving vascular access increases further. The caregivers available under these circumstances may have a very low level of training, such as that associated with the lowest categories of paramedic or firefighter, or the military combat lifesaver. Further, such caregivers often have limited opportunities to practise and retain their skills.

Substantial delays in administering the drugs and liquids can therefore result and, in many instances, vascular access cannot be attained at all. Severe injury to the patient, even death, can therefore result.

In such cases of serious circulatory shock and hemorrhaging, one suitable alternative to intravascular infusion is intraosseous (IO) infusion. In particular, the resuscitative fluid or drug solution is injected directly into the marrow of the patient's bone. Typically, the sternum, femur, tibia, or other long bone located near the skin is used. Intraosseous infusion also is sometimes used on newborns and small children when suitable blood vessels cannot easily be accessed. Intraosseous infusion requires the penetration by a needle or the like of the patient's skin and overlying tissue and outer cortical bone, to gain access to the interior bone marrow space.

Another need for accessing the bone marrow space arises when a bone marrow sample is to be drawn, or aspirated. Again, a needle or the like must penetrate the patient's skin and outer cortical bone to gain access to the marrow.

Although intraosseous infusion is considered a viable alternative to intravenous infusion, it has not met with widespread acceptance. Among the reasons for this are several practical problems relating to implementation.

One problem with intraosseous infusion is the practical difficulty of inserting the infusion needle or other device to the proper depth in the bone in order to access the marrow. In one typical approach to this problem in the past, a collar or other stop was fixed on the needle shaft to indicate by reaching the skin surface, that the needle had penetrated to a particular depth estimated to be within the marrow space. Intraosseous infusion devices which use the skin surface as the depth reference point include e.g. U.S. Pat. No. 4,969,870 to Kramer et al, U.S. Pat. No. 5,176,643 to Kramer et al, U.S. Pat. No. 4,469,109 to Mehl, U.S. Pat. No. 5,271,744 to Kramer et al, and U.S. Pat. No. 5,312,364 to Jacobs.

Other devices utilize a drill to thread the needle into place or require a significant amount of operator manipulation during insertion of the needle. See, e.g. U.S. Pat No. 1,523,068 to Hein, U.S. Pat. No. 2,773,500 and U.S. Pat. No. 2,773,501 to Young, U.S. Pat. No. 5,372,583 to Roberts et al, and U.S. Pat. No. 5,431,655 to Melker et al.

These techniques are not always effective, however, because they use the skin surface as the reference point or because they rely on the user to know the correct anatomical location, and to estimate the required depth.

Human subjects show considerable variability in the sizes and thicknesses of the walls of their bones, of the marrow spaces inside the bones, and of the depth of the layers of skin, muscle, and fat which make up the tissues overlying the bones. For example, skin and tissue thicknesses overlying the sternum, in one review, have been found to range from 3 mm to over 25 mm in total thickness. For the above reasons, using the skin surface as a reference point for the user to gauge depth of penetration, and marrow access may be both completely ineffective due to the low probability of placing the needle in a desired location, or unsafe due to the high probability of placing the needle in a hazardous location such as a tissue compartment, a bone growth plate, a nerve, a great vessel, or the heart.

Another typical approach to the problem of achieving correct placement of an intraosseous system has been to monitor the resistance to penetration of a conventional infusion/aspiration needle, see e.g. U.S. Pat. No. 4,469,109 to Mehl. This is not always an effective indicator of the needle's position within the bone, either. Generally speaking, the resistance is relatively high when the tip of the needle is moving through the outer cortical bone, and it decreases when the tip reaches the marrow space. The resistance increases again if the needle tip reaches the inner cortical bone, on the opposite side of the marrow. However, such variations in resistance can be very subtle and can vary substantially from one patient to another. Further, they require the user to advance the needle very slowly and with considerable skill, often with twisting, in order to not suddenly break through the bone and over-penetrate. Medical literature contains several reports of death caused by overpenetration of the sternum by infusion/aspiration needles when correct depth setting relied on monitoring penetration resistance and position. Accordingly, monitoring penetration resistance is not considered an effective technique for controlling penetration depth.

A second reason why intraosseous infusion has not met with widespread acceptance is the difficulty of dealing with forces on those parts of the apparatus that protrude above the skin, and with movements of the skin and tissue overlying the infusion site. In the past there has been no successful solution to this problem. These forces and movements may be transmitted to the fixed point where the system enters the bone. Additionally, the circumstances and environments of field and emergency conditions may include cardiopulmonary resuscitation of the patient, confused and violent physical activity around the patient, and rapid and rough movement of the patient on a battlefield or disaster scene, all of which will produce physical forces and tissue movements near the intraosseous infusion device, which may cause it to leak or come out of the bone. In particular, any intraosseous infusion system which passes through the skin into the underlying bone, and which is intended for use in field and emergency situations, must accommodate or resist large and forceful skin movements over the infusion site. A drawback of any intraosseous infusion device which protrudes above the surface of the body is that it will be exposed and sensitive to these forces and hence unsuitable for use in field and emergency conditions. Further, all intraosseous infusion devices connected by external tubing to sources of suction or infusion fluid and must be protected from forces which might be applied to the tubing and disturb the infusion site.

There is therefore a significant need for an intraosseous infusion or aspiration apparatus, and related method, that conveniently and accurately places the tip of an infusion/aspiration needle or tube within a patient's marrow space, for an effective infusion of liquid to, or aspiration of bone marrow from, a patient. It should be further appreciated that for emergency purposes there is a significant need for such apparatus and method to be fast, safe, effective and reliably usable by a caregiver with a low level of skills, under adverse conditions, and regardless of the thickness of skin and tissue overlying the infusion site.

SUMMARY OF THE INVENTION

The present invention is embodied in a novel intraosseous infusion/aspiration apparatus, and related method, which is fast, safe, effective and reliable in emergency and field environments, when used by caregivers including those with low levels of training and skill. The device is adapted to ensure that infusion fluids will be delivered to a precise target zone within the marrow of a patient's target bone, without a need to estimate the required penetration depth from the skin, without the need to precisely monitor the bone's resistance to the penetration, and regardless of the thickness of the skin, fat, muscle or connective tissues overlying the bone. This is done by relating the target zone of the bone marrow with the distal surface of the target bone and thereby avoids having to deal with relatively large variations inskin and tissue thickness.

In this disclosure, the terms "distal" and "proximal" are used according to the meanings common in anatomy and medical technology, that is, "distal" means farther from the centre of the patient, "proximal" means closer to the centre of the patient. The invention in one embodiment is directed to a low profile apparatus for intraosseous fluid infusion or aspiration of bone marrow of a patient. The apparatus is installed subcutaneously against a bone of the patient.

The invention is directed to a bone-installed apparatus for intraosseous fluid infusion or aspiration of bone marrow of a patient, comprising a fluid conduit having a distal end and a proximal end, the distal end of the fluid conduit being movable relative to the proximal end, the proximal end being installed in the bone of the patient.

In another aspect, the invention is directed to a bone-installed apparatus for intraosseous fluid infusion or aspiration of bone marrow of a patient, comprising: (a) a fluid conduit having a distal end and a proximal end; and (b) a bone stop means, a proximal side of the bone stop means impinging against a surface of the bone when the proximal end of the fluid conduit is located in underlying bone marrow.

The invention is also directed to a bone-installed apparatus for intraosseous fluid infusion or aspiration of bone marrow through the skin of a patient, comprising a fluid conduit having a distal end and a proximal end wherein the distal end is attached directly or indirectly to the skin of the patient, and the proximal end is located in the bone marrow, the fluid conduit being of sufficient length to allow a surplus of fluid conduit between its proximal end and its distal end when the skin has been moved to its limit of movement.

The apparatus in another embodiment comprises: (a) a bone penetration means with a proximal end and a distal end and lumen fluid transmission means therein extending from the proximal end to the distal end; (b) an applicator means which detachably engages the bone penetration means and enables an administrator to cause the proximal end of the bone penetration means to penetrate part of a bone and part of the underlying marrow of the patient; and (c) a fluid conveyance means which is connected to the lumen fluid transmission means at the distal end of the bone penetration means.

The bone penetration means and the proximal end of the applicator means can be sharp. The fluid conveyance means can be a flexible tubing. A distal end of the fluid conveyance means can be moveable relative to a proximal end of the fluid conveyance means.

The bone penetration means can have a low profile and when installed subcutaneously in the patient, the distal end of the bone penetration means does not protrude above the skin of the patient. The applicator means can be a handle and an associated rigid stylet, which can penetrate the interior of the fluid conveyance means, contact the bone penetration means, and enable an administrator to push the proximal end of the bone penetration means through surface bone and into the underlying marrow of the patient.

In another embodiment, the invention is directed to a low profile apparatus for intraosseous fluid infusion or aspiration of bone marrow of a patient, the apparatus being installed subcutaneously against a bone of the patient. The apparatus further comprises: (a) a bone penetration means with a proximal end and a distal end and lumen fluid transmission means therein extending from the proximal end to the distal end; (b) an applicator means which detachably engages the bone penetration means and enables an administrator to cause the proximal end of the bone penetration means to penetrate part of a bone and part of the underlying marrow of the patient; and (c) a bone stop means, a proximal side of the bone stop means impinging against the surface of the bone of the patient when the proximal end of the bone penetration means penetrates the surface bone and a part of the marrow of the patient.

The bone stop means can be located on a proximal end of the applicator means. The bone stop means can comprise a plurality of rods which can protrude from the proximal end of the applicator. The rods can encircle at least part of the distal end of the bone penetration means.

The applicator means can be hollow, elongated and open at one end. A stylet having a distal end and a proximal end can be located longitudinally within the hollow of the applicator means and the proximal end of the stylet can protrude from the hollow through the open end. The bone stop means can be located on the proximal end of the applicator means adjacent the open end.

The applicator means can be open on each side to provide a first proximal part and a second proximal part, the stylet being accessible through the openings on each side between the first proximal part and the second proximal part, and from the open end of the hollow applicator means. The bone stop means can comprise a pair of clusters of longitudinally extending rods, one of the pair of rod clusters being located at the proximal end of the first proximal part and the second of the pair of rod clusters being located at the proximal end of the second proximal part.

The tips of the first proximal part and the second proximal part can be moved together to support the stylet. The apparatus can include a protective covering which removably fits over the bone stop means.

The apparatus can also include a sliding stop means which fits on the plurality of rods, the sliding stop means having sharp, hollow proximal points which correspond in number with and fit over the number of rods, the hollow points enabling the plurality of rods to slide through the corresponding hollow proximal points.

The apparatus can include protector means which can be applied to the skin of the patient and cover and protect the bone penetration means and the fluid conduit means. The protector means can comprise a shell which can be convex on the distal side and concave on the proximal side. The shell can have an opening therein for enabling a fluid transmitting connector to be connected to a distal end of the fluid conduit means.

The length of the fluid conveyance means, which can be a flexible tubing, is sufficient to permit a distal end of the fluid conveyance means to be moved without disturbing the proximal end of the fluid conveyance means which is connected to the lumen fluid transmission means at the distal end of the bone penetration means, that is installed subcutaneously in the patient. The fluid conveyance means is of sufficient length to enable a surplus (slack) of fluid conveyance means to be present between the distal end of the bone penetration means and the distal end of the fluid conveyance means detachably connected to the fluid transmitting connector. Thus if a tension force is exerted on the fluid transmitting connector, the surplus will prevent the bone penetration means being pulled loose.

The proximal side of the perimeter of the shell can have thereon an adhesive which can enable the perimeter of the shell to be affixed to the skin of the patient. The proximal side of the perimeter of the shell can include a layer of foam between the perimeter of the shell and the adhesive, for accommodating variations in anatomical topography of the patient.

The fluid transmitting connector can also be a flexible tube. The proximal end of the connector means can have thereon a fitting that detachably connects to a fitting on the distal end of the fluid conveyance means. The distal end of the connector means can have thereon a fitting which detachably connects with an intravenous tube fitting. The fluid transmitting connector can be a combination of a rigid tube and a flexible tube.

In a further embodiment, the invention is directed to a low profile bone penetration apparatus for subcutaneous intraosseous fluid infusion or aspiration of bone marrow of a patient. The apparatus comprises: (a) a sharp proximal end for penetrating surface bone and a portion of underlying marrow of the patient; (b) a surface for impinging against a bearing surface of a detachable applicator; and (c) a hollow end connected internally by a lumen with the sharp proximal end for enabling a fluid conveyance means to be detachably connected to the hollow distal end. The total length between the hollow distal end and a reference point distal to the proximal end being less than the depth of tissue and skin overlying the bone of the patient so that the bone penetration apparatus when installed in the patient resides completely subcutaneously in the patient. A port can be located at the proximal end and connected with the lumen.

Alternatively, a port or plurality of ports can be located in the sides adjacent the sharp proximal end at a location which is adjacent to bone marrow when the bone penetration apparatus resides subcutaneously in the patient, said side port or ports connecting with the lumen.

In a further embodiment, the invention is directed to a method of intraosseous infusion of fluid into bone marrow or aspiration of bone marrow of a patient comprising: (a) a first step of locating an appropriate site on a suitable target bone of the patient; (b) a second step of positioning a low-profile bone penetration means with a lumen therein subcutaneously in the patient using a detachable applicator, a proximal end of the bone penetration means being positioned at a precise marrow depth by reference to the distal surface of the target bone, the distal end of the bone penetration means being below the skin of the patient, the bone penetration means having connected at its distal end a fluid conduit means; (c) a third step of removing the applicator; and (d) a final step of attaching to the distal end of the lumen of the bone penetration means a source of fluids for infusion of fluid into the bone marrow or a source of suction for aspiration of bone marrow.

The method can include an additional step of installing a protection means over the bone penetration means and the fluid conduit means. The source of fluids can be attached to the distal end of the fluid conduit means and the fluid conduit means has sufficient slack therein to enable the protector and the distal end of the fluid transmissions to move with the skin of the patient and not disturb the bone penetration means in the target bone.

In a further aspect, the invention pertains to a method of determining proper depth of penetration of a bone penetration means into bone marrow of a patient by relating the bone marrow depth with the distal side of a bone of a patient in which the bone penetration means is installed.

BRIEF DESCRIPTION OF THE DRAWINGS

In drawings which illustrate specific embodiments of the invention, but which should not be construed as restricting the spirit or scope of the invention in any way:

FIG. 4 represents a side view of the applicator.

FIG. 4a represents an end view of the applicator shown in FIG. 4.

FIG. 5 represents a side view of the infusion tube.

FIG. 6 represents an enlarged exploded isometric quarter section view of one embodiment of a bone penetration means device, which may be located at the proximal end of the infusion tube of FIG. 5, and the applicator tip above the bone penetration means device.

FIG. 7 represents an enlarged exploded isometric quarter section view of an alternative non-coring bone penetration means device, with side ports, which may be connected to the proximal end of the infusion tube of FIG. 5.

FIG. 8 represents a side partial section view of the proximal ends of the bone penetration means device and infusion tube, being placed into the distal bone and part of the marrow of a patient, by the applicator.

FIG. 13 depicts a side view of the applicator and infusion tube with two sliding skin port devices slidably fitted over two separate sets of bone stop rod clusters.

FIG. 14 depicts an enlarged isometric view of a sliding skin port on a bone stop rod.

FIG. 15 depicts a side partial section view of a bone stop rod and a sliding skin port after it has cut through skin.

FIG. 16 depicts a sequential side partial section view of a sliding skin port and bone stop rod when a downward force has been applied to the skin port and bone stop rod.

FIG. 17 depicts a bottom view of a sliding skin port with five sharp tubes for fitting on five rods of a rod cluster, as illustrated in FIG. 13.

DETAILED DESCRIPTION OF PREFERRED EMBODIMENTS OF THE INVENTION

Figure 1:
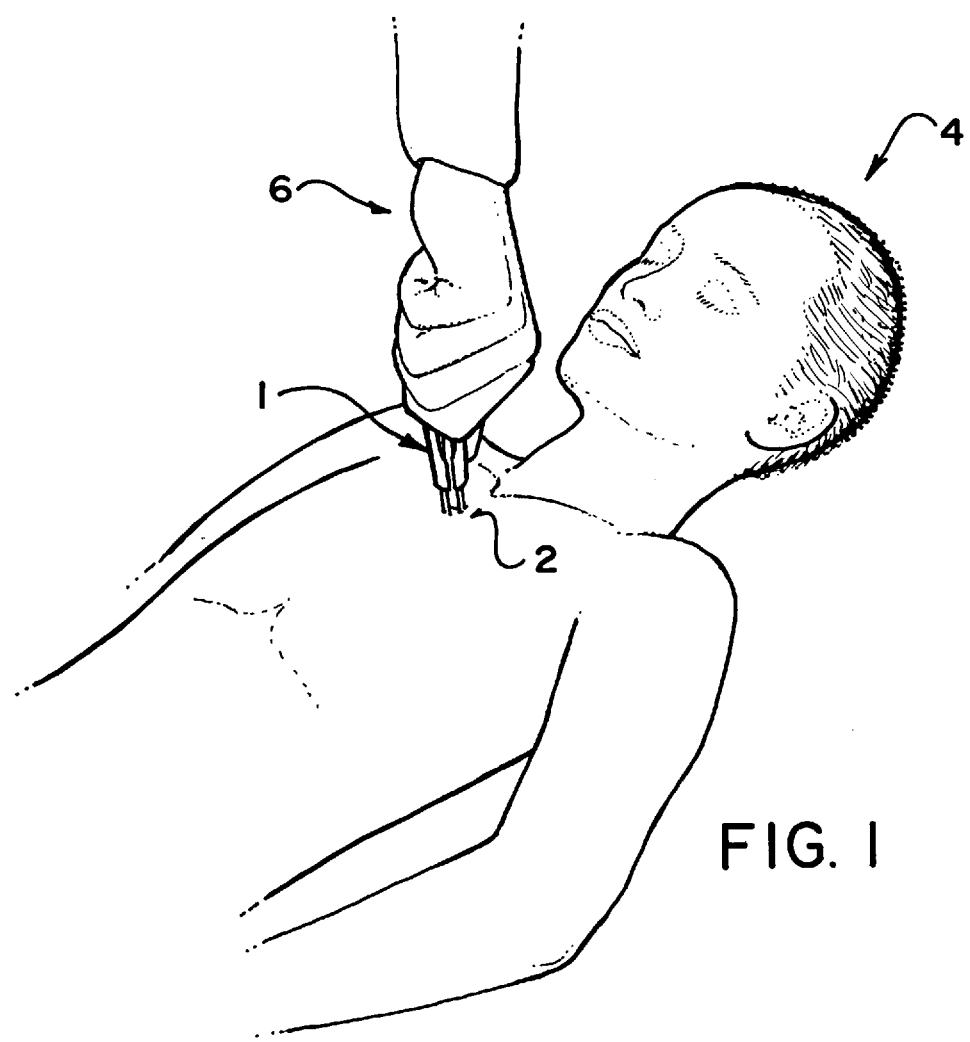
FIG. 1 depicts a perspective view of the invention being used by a paramedic to gain vascular access through the patient's sternum.

In this disclosure, the terms "distal" and "proximal" are used according to the meanings common in anatomy and medical technology, that is, "distal" means farther from the centre of the patient, "proximal" means closer to the centre of the patient.

In one aspect, the apparatus includes a removable applicator configured to allow the infusion/aspiration tube to be introduced into the correct position in the bone, through the tissues and skin overlying the infusion/aspiration site, an infusion/aspiration tube adapted for correct placement in the bone into which the liquid is to be infused, or from which the marrow is to be aspirated, and a protector system to isolate the apparatus from skin motion and external forces.

The applicator includes a handle for allowing the user to advance the proximal end of the infusion/aspiration tube through the skin and overlying tissues and through the cortical bone into the marrow space, and a stylet for transmitting the pushing forces from the handle to the bone penetration means. The applicator and the infusion/aspiration tube can be fitted together as an assembly for the purpose of introducing the infusion/ aspiration tube into the correct location in the patient. A feature of the invention is that the applicator can be removed from the infusion/ aspiration tube for the purpose of infusing or aspirating fluids through the infusion/aspiration tube.

The infusion/aspiration tube includes a connection fitting, a length of flexible tubing, and a bone penetration means. The fitting is attached to the distal end of the flexible tubing and is adapted for receiving liquid to be delivered to the patient's bone marrow and for supplying the liquid to a bore in the tubing. The proximal end of the tubing is connected to the bone penetration means and is adapted for delivering the liquid to a bore in the bone penetration means. Alternatively, these parts may be used for delivering bone marrow to outside the apparatus during aspiration.

In a separate and independent embodiment of the invention, the apparatus includes a bone stop adapted to ensure that the sharp tip of the bone penetration means is placed in the marrow at a precise location and depth relative to the outer surface of the outer cortical bone or the outer surface of the periosteum. The bone stop can comprise part of the bone penetration means or part of the applicator. The relative positions of the bone stop and the tip of the bone penetration means are determined to ensure that the tip of the bone penetration means is at the precise target location in the bone marrow, when the bone stop has contacted the bone or periosteum. The tip of the bone penetration means can be readily advanced through the skin and tissue and into the target bone. The bone stop can be readily advanced through the skin and tissue overlying the bone, but will stop and resist further penetration when the bone stop contacts the bone or periosteum. The apparatus is thus much more reliable than prior art devices because it uses the distal surface of the bone or periosteum instead of the surface of the skin as the reference point for achieving a proper bone penetration depth which is sufficient to reach the marrow, but which is not sufficient to reach the inner cortical bone, a cause of potential serious injury.

A separate and independent feature of the invention is that the bone penetration means is of a low profile and is thereby subcutaneous to remove it from the effects of external forces and skin movements which would otherwise cause the intraosseous infusion device to enlarge the hole through which it penetrates the bone, or to leak, or to fall or pull out. In particular, the bone penetration means is short enough so that when the device is correctly positioned subcutaneously in the patient, the entire bone penetration means is below the surface of the patient's skin, and is below much of the tissue under the skin. Only the flexible infusion tube emerges through the skin. The distal end of the flexible infusion tube can be moved about without dislodging the bone penetration means.

In a separate and independent embodiment of the invention, the bone stop comprises a multiplicity of thin, sharp protrusions (rods or needles) which can easily penetrate the patient's skin, but which are extremely difficult to push through the bone. In another embodiment, the protrusions are in the form of a cluster of ten parallel needles mounted in and protruding from the proximal end of the applicator handle. A depth reference plane is defined by the plane of the sharp tips of the needles in the needle-cluster. Thus the needle-cluster bone stop can be advanced through the skin without the need for any incision to be made prior to insertion of the infusion tube. As many sharp protrusions may be used as are needed to provide adequate protection against penetrating the bone. The tips of the protrusions can be made of a material (for example, a plastic) which is sufficiently strong to penetrate skin, but not sufficiently strong to penetrate bone.

In another feature of the invention, the applicator includes a means for ensuring that the bone stop protrusions travel easily through the skin, but do not enter the outer cortical bone. In one embodiment, this is accomplished by a sliding skin port with a sharp proximal tip that pierces the skin, and comes to a stop a preset distance below the surface of the skin. The sliding skin port includes a hypodermic type needle tip with a lumen and a skin stop that makes contact with the surface of the skin when the hollow needle tip has advanced completely through the skin. The sliding skin port can move relative to the bone stop protrusion which allows the bone stop protrusion (which can be blunt at its proximal end) to be advanced through the hole in the hollow sliding skin port. In this way, the bone stop can be advanced through the skin and overlying tissue because the resistant skin has been penetrated by the sharp end of the sliding skin stop.

A further embodiment of the invention is a protective covering which protects the sharp tips of the bone stop means, the sharp tip of the bone penetration means and the sharp tip of the stylet from damage. The protective covering protects the user from injury. The protective covering may comprise a cylinder which fits closely around the bone stop, such that when the handle of the applicator is squeezed into a fully closed position against the stylet, the protective covering drops off, thereby exposing the sharp tips ready for use.

Yet another separate embodiment of the invention is that the infusion/aspiration tube is flexible. It is connected at its proximal end to the distal end of the subcutaneous bone penetration means and at its distal end to a connection means. This allows connection of the tube to a fitting of a protector system or directly to sources of fluid to be infused into the patient, or sources of suction for aspiration. In the case of direct connection to fluid sources, the connection means will typically be a Luer™ fitting. The flexible tubing passes from the bone penetration means, firmly fixed in the bone, through the overlying tissue and out the hole in the skin which has been made at the time of inserting the bone penetration means and infusion tube in the patient. Because the tubing is flexible and absorbs movement, it allows forces on the patient's skin to produce large skin or tissue movements above the subcutaneous bone penetration means, without transmitting these potentially adverse forces or movements to the bone penetration means below the skin. If the tubing were rigid or not sufficiently flexible, this could not happen, and the bone penetration means would be dislodged.

In a further embodiment of the invention, the apparatus includes a protector means. The protector means includes a hard shell, a fluid transmitting connector to provide a fluid path between an IV line and the infusion tube, a foam layer, and an adhesive layer that attaches the foam layer securely to the skin.

The hard shell, which is concave on its proximal side, protects the infusion tube. The shell is sufficiently strong to withstand applied external forces, for example from hands, during manipulation of the patient, or a cervical collar which may rest on top of the hard shell. The shell may be transparent and thus conveniently allow the infusion site and infusion tube to be viewed during use. It also keeps the infusion site clean and protects it from infection.

The foam layer is another feature and embodiment of the invention. It is located on the perimeter of the proximal side of the hard shell and consists of a layer of foam of sufficient thickness and compressibility to accommodate expected local anatomical topographical variations from patient to patient. This thus allows the adhesive layer to make contact with the skin around the entire perimeter of the protector means by accommodating differences in topographical profile between the surface of the chest, or other anatomical part, and the underside of the hard shell.

An adhesive layer attaches the perimeter of the proximal side of the protector means (protector) to the skin. The adhesive layer has a stoppable backing that protects it prior to use. The adhesive layer is a highly sticky substance that readily bonds to shaved or unshaved skin that has or has not been cleaned. The bonds between the foam layer, the hard shell, and the fluid transmitting connector are sufficiently strong that tension forces applied to the infusion or aspiration supply lines are transmitted through the fluid transmitting connector, the protector shell, the foam layer and the adhesive layer to the skin, instead of being transmitted through the infusion tube to the bone penetration means. The bone penetration means thus stays put.

A further embodiment of the invention is the inclusion of slack in the flexible tubing. When the infusion tube is attached to the proximal fitting of the fluid transmitting on the protector shell, and the proximal side of the protector is adhesively attached to the skin, there is sufficient slack in the infusion tube and sufficient space under the shell, that movements of the shell, caused by movements of the skin, or by forces applied directly to the shell, take up the slack in the infusion tube rather than being transmitted to the infusion tube and bone penetration means.

The fluid transmitting connector which passes through the protector also provides a pathway for the fluid to pass from the intravenous (IV) line to the infusion tube and into the bone marrow. The proximal end of the fluid transmitting connector connects to the distal end of the infusion tube. This connection can be made easily due to the orientation and position of this connector with respect to the protector shell. The distal end of the fluid transmitting connector normally consists of a slip-fit (non-locking) Luer which mates with the male Luer fitting on the proximal end of the IV line. The slip fit allows the connection to act somewhat like a mechanical safety fuse so that an excessive force on the IV line, for example produced by someone tripping on the line, or having the line caught during transport, will cause this connection to come apart, rather than causing the excessive forces to be transmitted to the patient's skin, or the infusion tube, or the bone penetration means.

In another embodiment of the invention, the fluid exit ports from the bone penetration means may be located either at the proximal tip or on the sides of that portion of the bone penetration means that penetrates through the cortical bone and into the bone marrow. When the port is located at the proximal tip, the proximal tip of the stylet is designed so that the port will be plugged during insertion by the proximal tip of the stylet which comprises part of the applicator. This prevents a core of bone from entering and plugging the lumen of the bone penetration means. When the ports are located on the sides of the bone penetration means, they need not be plugged with a tip of the stylet, as cortical bone will not laterally enter the ports during the insertion process. However, with side ports, it is important to ensure that they are correctly positioned so that they are adjacent bone marrow and not bone, when the bone penetration means is installed.

In a further embodiment of the invention, the bone stop is integral to the applicator handle and comprises a bone stop which will easily penetrate the patient's skin, but which will be extremely difficult to push through the bone. Thus it serves to stop further insertion of the bone penetration means when the bone penetration means has reached the correct location (marrow depth) relative to the surface of the cortical bone. The applicator handle has means thereon to support the stylet, thereby allowing a very thin stylet, which is in the form of a slender rod, to apply sufficient installation forces to the bone penetration means. The bone stop is removed from the patient when the applicator and stylet are withdrawn from the infusion/aspiration tube, thereby leaving the bone penetration means in place in the bone. This allows the bone penetration means to have a very low profile under the skin, and avoids the need to leave a bone stop in place during infusion through the flexible tube.

A preferred method of intraosseous infusion comprises the following steps. When the target bone for the device is the sternum, the intended infusion site is located by simply palpating the deep notch at the top of the sternum (present in all human beings), and measuring one finger width down from it on the centre line of the chest. This procedure enables easy and accurate targeting of the desired location on the manubrium. The complete apparatus (that is the applicator and bone stop, and infusion/aspiration tube with bone penetration means fitted together) is positioned with the sharp tip of the stylet, bone penetration means and infusion tube over the intended infusion site. The assembly is pushed by the administrator through the patient's skin by manual force until the sharp tip of the bone penetration means and infusion tube and the sharp tips of the bone stop have penetrated the patient's skin. Further force is applied by the administrator until the sharp tip of the bone penetration means has penetrated the outer cortical bone and the depth reference plane defined by the sharp tips of the bone stop rods has impinge on the surface of the outer cortical bone or the periosteum covering it, preventing further advancement. The bone stop is known to have reached the correct bone and marrow penetration position when continued application of moderate force by the administrator no longer advances the assembly through the tissue and bone. Because of the spatial relationship in the apparatus between the fluid delivery ports and the bone stop has been predetermined, the fluid delivery ports will now be positioned at the precisely correct location in the patient's marrow space. When this position has been reached, the applicator handle is pulled back, thereby removing the applicator and stylet from inside the infusion tube. A strain relief protector may then be attached to the infusion tubing and affixed by adhesive to the skin of the patient. Liquid can then be infused into the marrow space, or marrow aspirated from it, through one or more ports located in the bone penetration means at the tube's proximal end.

As is apparent from the description of the intraosseous infusion device and the related method of use, the goals of the invention are readily satisfied. An intended infusion site in the sternum can be quickly and accurately located. The infusion tube can be quickly and accurately placed at the correct depth in the bone, regardless of the thickness of overlying tissue, with a simple action of pushing in the assembled apparatus and pulling out the applicator. If necessary, these steps can be accomplished with one hand, in the dark. A protector system adequate for all expected dislodging forces encountered in the field can be quickly placed by users with a low level of skill and training. The resulting infusion system is immune to large forces and movements of the skin over the infusion site.

SPECIFIC EMBODIMENTS AND PREFERRED MODE

With reference now to the drawings, there is shown in the drawings a first embodiment of an intraosseous infusion apparatus for infusing a liquid (e.g., whole blood, lactated Ringers, hypertonic saline dextran, or a drug solution) into the marrow of a patient's bone. FIG. 1 illustrates a perspective view of the apparatus 1 (which is a combination of the applicator 10 and tube 30 shown in FIG. 2) being inserted into the sternum 2 of a patient 4 by a paramedical user 6. The apparatus is particularly useful in rapidly, safely and reliably providing vascular access for infusion of the liquids into patients for whom there is a difficulty in utilizing the more common peripheral intravenous infusion. This may be due, for example, to low blood pressure brought on by severe circulatory shock or hemorrhaging or by small vessel size. The apparatus is particularly useful in field and emergency situations involving extreme environmental conditions and caregivers with a low level of training, practice or retention of skills. Suitable bones for access include, for example, the manubrium (upper part of sternum), distal femur, proximal tibia, and iliac crest, which are all relatively large and located very close to the skin. Although these particular bones are preferred, any red marrow site on the patient can be used. The device is particularly useful for providing infusion into these bones, regardless of the thickness of skin and tissue overlying them.

Figure 2:
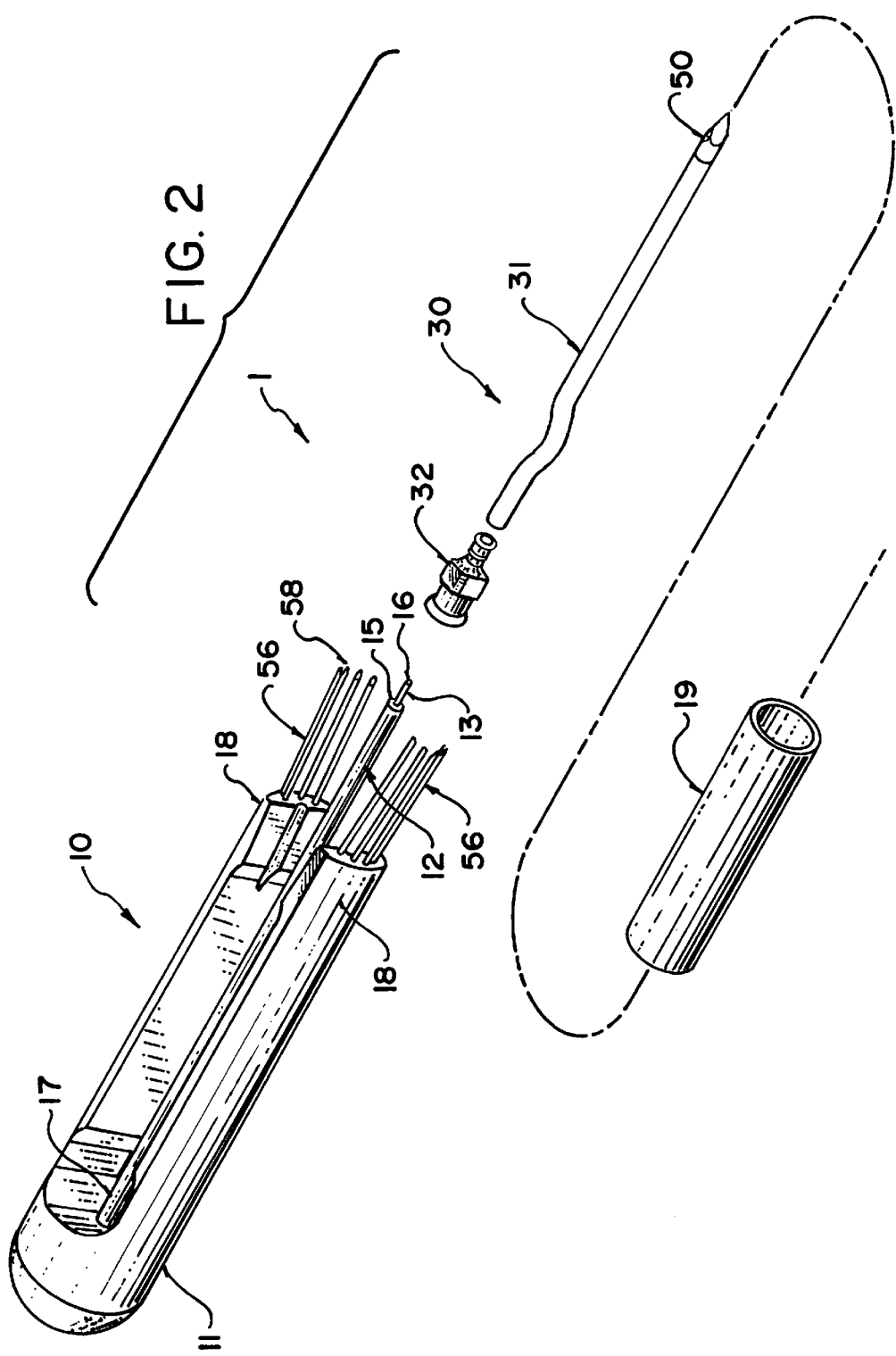
FIG. 2 represents an exploded perspective view of the applicator, infusion tube and protective covering.

FIG. 2 depicts an exploded perspective view of the principal parts of the apparatus 1, including the applicator, infusion tube and protective covering. The apparatus 1 includes an elongated, flexible infusion tube 30 (flexibility is indicated by the curved area in the tubing) through which fluid is to be infused into the marrow, and a removable applicator 10. The cylindrical protective covering 19 is hollow. The manner in which it is fitted over the rod cluster bone stop 56 is indicated by dotted lines. The infusion tube 30 includes a bone penetration means 50 and flexible tubing 31 and a fitting means 32 for connecting the tubing 31 to a source of fluid to be infused, or to a protector system, as described later.

The applicator 10 is constructed of a protective handle 11 and an internal rigid slender rod-like stylet 12 which fits inside the tube 30 (see FIG. 3) and, by being rigid, transmits linear insertion forces from the handle 11 to the bone penetration means 50 to enable insertion of the bone penetration means 50 into the patient. The stylet 12 includes a lower end 13 which may have a means 15 for engaging bone penetration means 50 and a remote tip 16, which may be sharp. The design of the proximal end of the stylet 12 is tailored to the type of bone penetration means that is used (see FIGS. 6 or 7).

In FIG. 2, the flexible tubing 31 has a lumen through which fluids are delivered or marrow contents extracted. The distal end of the tubing 31 is attached to a connection means 32 which allows the infusion tube 30 to be connected to a protector system (not shown, but see FIGS. 9–12) or to a source of vacuum (not shown) for extracting marrow contents, or to a source of fluid for infusing the fluid into the patient. The tubing 31 is sufficiently flexible that movements of its distal portions including connection means 32 are not transmitted to its proximal end which is connected to bone penetration means 50.

In FIG. 2, it may also be seen that liquid may be delivered to the tubing via a connection means 32 located at the distal end of the flexible tubing 31. The fitting means 32 may be adapted to connect with a protector system, or it may be adapted for connection to any conventional infusion device (not shown in the drawings), such as an autoinjection canister, gravity feed bag, or syringe.

Figure 3:
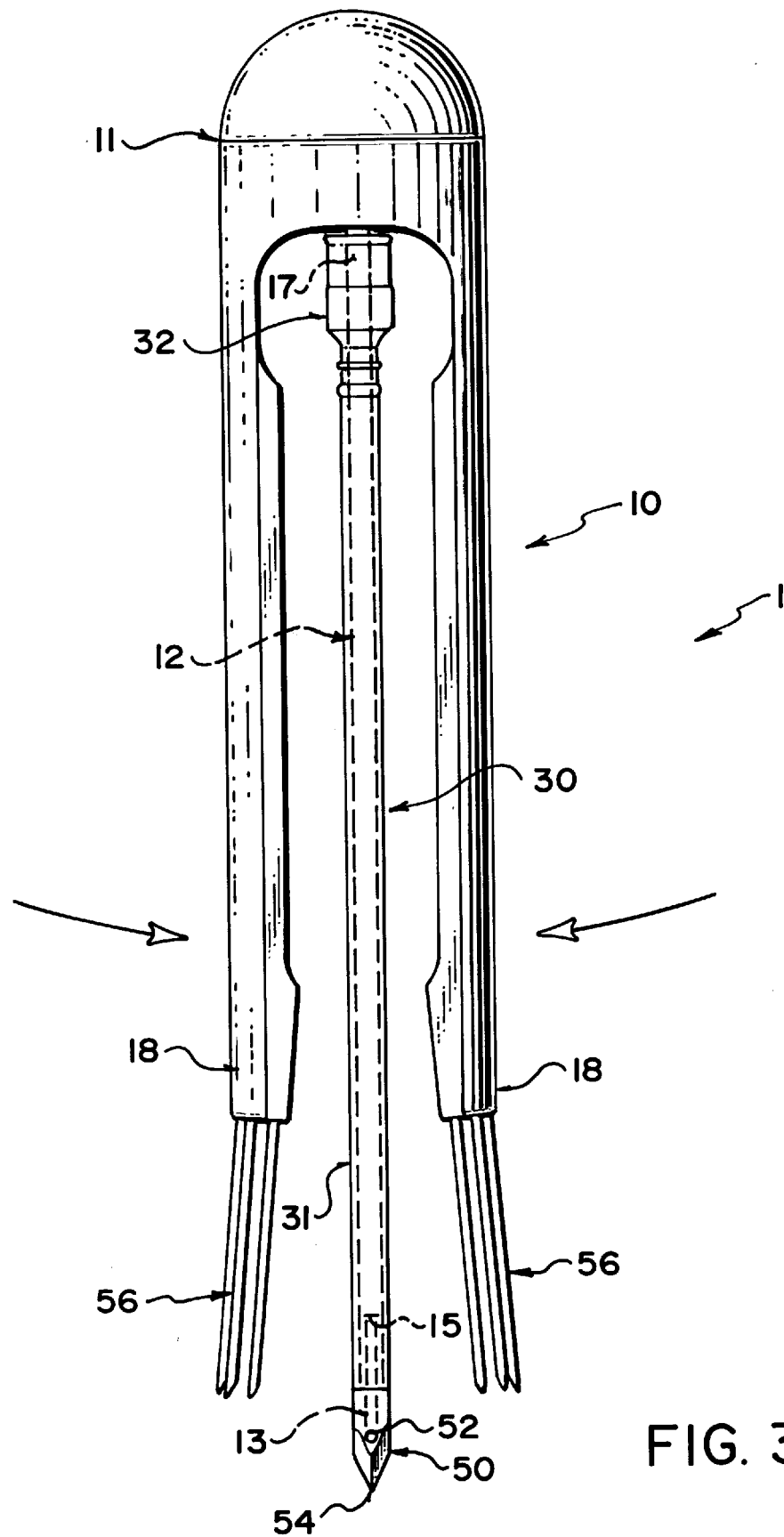
FIG. 3 represents a side view of the applicator and infusion tube, assembled ready for use.

FIG. 3 illustrates a side view of the applicator assembly 1 made up of applicator handle 11, with needle cluster bone stop 56, flexible tubing 31, and bone penetration means 50, ready for insertion in a patient. The rigid stylet 12 (not visible) penetrates inside the tube 31 to the bone penetration means 50. The applicator handle 11 is removed after the bone penetration means 50 has been installed in the sternum (or other accessible bone) of the patient. The flexible tube 31 with connecting means 32 is then free to flex.

Since the stylet 12 is long and slender (typically constructed of stainless steel), it requires lateral support in order to withstand bone penetration means 50 installation forces without buckling or bending. This lateral support is provided by the administrator squeezing the two proximal tips 18 of the handle 11 together so that they impinge on and laterally support the stylet 12 when the administrator is applying bone penetration means 50 installation force on the handle 11. This action is illustrated by arrows.

FIG. 4 illustrates a side view of the applicator 10. It is constructed of a hollow handle 11 rounded at the distal end for ease of holding by an administrator, a rod-like stylet 12 in the interior space of the handle 11 and proximal end 18, and a pair of needle cluster bone stops 56 (five needles on each side are typical). The lower proximal end 13 of the stylet 12 has a means 16 for engaging the bone penetration means 50 to push it through the skin 71 and overlying tissue 72 and to push the proximal end 53 of the bone penetration means (not shown but see FIGS. 6 or 7) through the outer cortical bone 74 into the marrow 70. The handle 11 connected to an upper end 17 of the stylet 12 can be manually pushed downwardly by the administrator to force the tip 16 of the stylet 12 (which is sharp if a bone penetration means of the design illustrated in FIG. 6 is used), or the blunt tip if the sharp tip 54 of the bone penetration means of the design shown in FIG. 7 is used, into the patient's skin 71 and overlying tissue 72 and subsequently through the outer cortical bone 74 into the marrow 70 (see FIG. 8).

Specifically, the handle 10 is configured so that it is bifurcated with two branches, the proximal ends 18 of which can be squeezed together into a closed position, or allowed to spring open into a natural open position. The handle 10 must be squeezed or held closed to retain it in the closed position. It will return to an open position if that constraint is removed. The handle 10 can also be retained in a nearly closed position by the presence of the protective covering 19 around the bone stop means 56. By squeezing the handle 10 together into the fully closed position, the protective covering 19 can be dropped off. Also, when the handle 10 is in the fully closed position, half cylinder grooves (visible in FIG. 4a) formed on the inside of each of the proximal ends 18 of the handle 10 form a stylet support and can provide firm lateral support to the slender bendable stylet 12.

FIG. 4a illustrates an end view of the applicator FIG. 4, and shows the cross-sectional construction of the semicircular proximal ends of stylet support 18, and needle cluster bone stops 56. The facing semicircular grooves which impinge and support the stylet 12 when the ends 18 are closed together, are also shown. The stylet 12, and stylet tip 13 are shown centrally disposed.

FIG. 5 represents an enlarged side view of the overall flexible infusion tube 30. The infusion tube has a Luer type fitting 32 at its distal end and a bone penetration means 50 (with side ports 52 of the style shown in FIG. 7) at the proximal end. The tube 31 is flexible as indicated by the curved mid-portion. The fitting 32 is adapted to be connected to a fitting (see FIGS. 9 and 10) or to a source of infusion fluids.

FIG. 6 depicts an enlarged exploded isometric quarter section view of one embodiment of a bone penetration means device which may be connected to the proximal end of the infusion tube 30 of FIG. 5. FIG. 6 also shows the applicator stylet 12 and tip 13 above the bone penetration means 50. As seen in FIG. 6, the upper (distal) end of tip 13 of the stylet 12 has a shoulder 15 which engages the shoulder 55 on the distal end 57 of the bone penetration means 50 and enables the administrator to push the bone penetration means 50 through the skin 71 and overlying tissue 72 (see FIG. 8). In this way, the proximal end 54 of the bone penetration means 50 is pushed through the outer cortical bone 74 into the marrow 70. A handle 10 connected to the upper distal end of the stylet 12 (see FIG. 2) can be manually pushed downwardly to force the sharp tip 16 of the stylet 12, and the relatively sharp tip 54 of the bone penetration means 50 into the patient's skin 71 and overlying tissue 72 and through the outer cortical bone 74 into the marrow 70. A scalpel is not necessary for cutting a small slit in the patient's skin to facilitate entry of the bone penetration means 50 and permit the bone stop 56 (see FIG. 4) to bear against the exterior of the bone.

FIG. 7 is an enlarged exploded isometric quarter section view of an alternative non-coring bone penetration means device, with side ports 52, which may be connected to the proximal end of the infusion tube 30 of FIG. 5. In the two designs of bone penetration means shown in FIGS. 6 and 7, bone penetration means 50 includes a hollow interior 51 or lumen and a proximal exit port 52 (FIG. 6) or side ports 52 (FIG. 7) through which fluid may be infused into the marrow. The bone penetration means 50 illustrated in FIG. 7 includes a proximal end 53 that projects through the outer cortical bone into the marrow, and includes a sharp, proximal tip 54 and a distal hollow stylet receiver 55 adapted to receive forces transmitted to it through the shoulder of the stylet 12 with a blunt tip 13 from the hand of the paramedic 6 inserting the bone penetration means 50 into the bone of the patient. The bone penetration means 50 includes a cylindrical distal end 57 which is adapted to connect with the hollow interior of the proximal end of flexible tubing 31 (not shown but see FIG. 5).

In the design of bone penetration means 50 shown in FIG. 7, it is important that the lateral ports 52 are located so that they are adjacent bone marrow, and not bone, when installed in the patient as shown in FIG. 8. The bone penetration means 50 of the design shown in FIG. 6 with the port 52 in the proximal end, does not have this design requirement since the proximal end of the bone penetration means 50 is always in the bone marrow 70 when correctly installed.

FIG. 8 represents a side partial section view of the proximal ends of the bone penetration means device and infusion tube, being placed into the distal bone and part of the marrow of a patient, by the applicator. Specifically, FIG. 8 shows the apparatus 1 in a position where the proximal sharp end 54 of the bone penetration means 52 has penetrated the cortical bone 74 and into the bone marrow 70. As seen in FIG. 8, the proximal end of the bone stop 56 which consists of two clusters of parallel needles on either side and somewhat distal of bone penetration means 50, has come to a stop against cortical bone 74. The bone stop reference plane 58 of the tips of the needles is a feature of the bone stop 56 and consists of a planar surface defined by the points of the needles of the bone stop 56. This plane 58 is designed to contact the cortical bone 74 or periosteum. By relating the distance between this reference plane 58, the precise depth of the bone penetration means proximal end 53 and exit ports 52 in the bone marrow 70 can be consistently applied. The bone stop 56 is comprised of parallel needle cluster means which can be readily advanced through the patient's skin 71 and through the tissue 72 overlying the bone, but cannot readily be advanced through the cortical bone 74.

The function of the bone stop is clearly illustrated in FIG. 8 which shows a side partial section view of the apparatus in a position where the proximal end 52 of the bone penetration means has penetrated the cortical bone 74 into the marrow 70. The bone penetration means 50 cannot be pushed past the point where the bone stop reference plane 58 has contacted the surface of the cortical bone 74, unless a highly unusual extraordinary force is applied to the handle 11.

In the past, it was difficult to determine precisely when the infusion device, e.g., a needle or threaded tube, had reached the marrow space 70. Frequently, in the case of an infusion needle, the needle tip would be stranded in non-bone tissue either short of or beyond the bone. The latter situation of projecting the needle beyond the bone and into the interior of the patient could be particularly dangerous because of the possibility of puncturing the heart or a major artery in the case of the sternum. On the other hand, if the port of the needle or other device was in the bone, but not in the marrow space (e.g., if it was in the outer 74 or inner 75 cortical bone), then infusion was difficult, if not impossible, because of the cortical bone's density. Until the development of the subject invention, and the unique concept of relating bone marrow depth to the surface of the bone, no convenient, reliable technique has been known for ensuring that the tip of the infusion device was properly positioned within the marrow space.

In accordance with the invention, a proper positioning of the exit ports 52 at the proximal end 53 of the bone penetration means 50 is ensured by providing a bone stop 56 which specifies that the exit ports 52 of the bone penetration means are placed in the marrow 70 at a precise location (depth) relative to the outer surface of the outer cortical bone 74 or the outer surface of the periosteum 73 (see FIG. 8). The proximal end of the needle cluster bone stop 56 provides an automatic depth reference plane 58 for placement against the outer cortical bone 74 or outer periosteum 73 of the bone into which the liquid is to be infused. When the apparatus has been placed by the administrator in its correct position in the patient, the bone stop depth reference plane 58 will be in direct contact with either the periosteum 73 or the outer surface of the outer cortical bone 74 of the patient. Then, the axial distance between the bone stop reference plane 58 and the fluid delivery ports 52 ensures that fluid will be delivered to the correct location (depth) within the marrow space 70. The overall lateral effective area of the bone stop 56 prevents the stop from being pushed through the bone 74 under ordinary force.

The lateral effective area provided by the two needle clusters of the bone stop 56 can be made of a sufficient size and width to provide adequate protection against penetrating the bone. Note that instead of needles, blunt rods can be used to form the bone stop. Thus, with proper sizing, number of needles or rods, and application of moderate force by the administrator, the apparatus will not advance further into the cortical bone.

Intraosseous infusion systems are usually exposed to large external forces and associated movements of the skin 71 and tissue 72 in the vicinity of the infusion site. Such movements can arise accidentally, or from other procedures such as chest compression, transport of the patient, defibrillation, or the need to splint or immobilize wounds. In the past, these forces and tissue movements could be sufficiently severe to cause the infusion needle or system to move within the bone, and to enlarge the hole through which they entered the bone, thus causing fluid leakage or inadvertent removal of the intraosseous infusion system. No prior technique is known for effectively isolating the device from skin and tissue movements.

Figure 9:
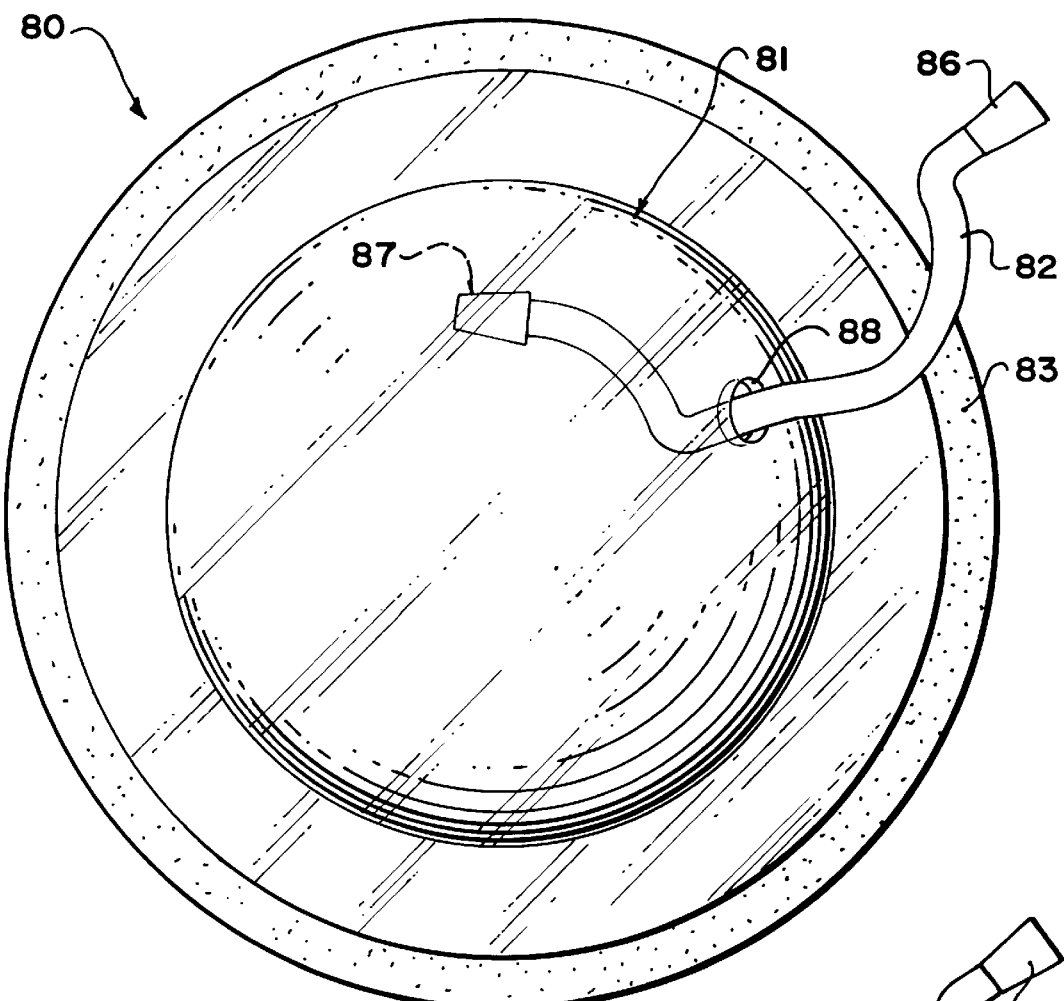
FIG. 9 represents a plan view of the protector.
Figure 10:
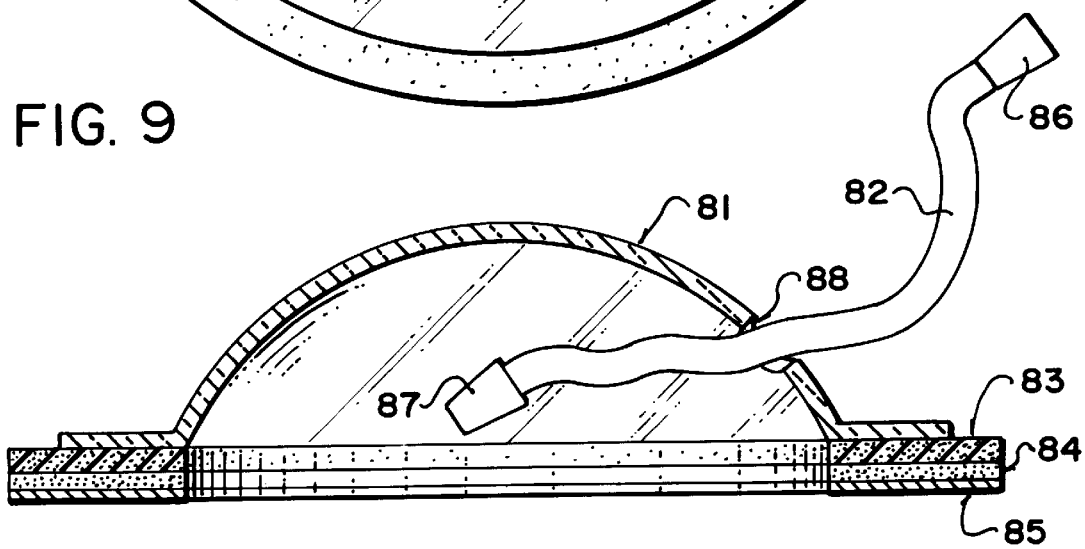
FIG. 10 represents a side partial section view of the protector.

FIG. 9 and FIG. 10 show plan and partial side section views of the protector system 80, which protects the bone penetration means and tube (not shown), and isolates them from extraneous movement and forces. The protector 80 includes a hard, clear concave/convex shell 81 that protects the infusion site and the infusion/aspiration tube from external forces. The protector 80 also includes around its proximal perimeter a compressible foam layer 83 composed of a layer of foam sufficiently thick and supple to accommodate anatomical topography variations around the infusion site under the perimeter of the shell 81. A sticky adhesive layer 84 on the proximal side of the foam layer 83 attaches the foam layer 83 to the patient's skin. Prior to use, the sticky adhesive layer 84 is covered with a protective strippable backing 85 that can be easily removed during application of the protector 80 to the patient's skin. The protector 80 also includes a flexible fluid transmitting connector tube 82 which provides a fluid pathway between the infusion/aspiration tube 30 (not shown) and the infusion device that is to be attached to the system for infusing or aspirating fluids. The fluid transmitting connector 82 includes at its proximal end a fitting 87 which is suited for connection to the corresponding fitting of the infusion/aspiration tube (not shown), and at its distal end a fitting 86 suitable for connection to sources of fluid to be infused, or sources of suction for aspiration. Also seen is a hole 88 in the hard shell 81 that allows the fluid transmitting connector 82 to pass through the shell 81, thereby enabling a fluid connection to be made between the outside and the inside of the shell 81.

Figure 11:
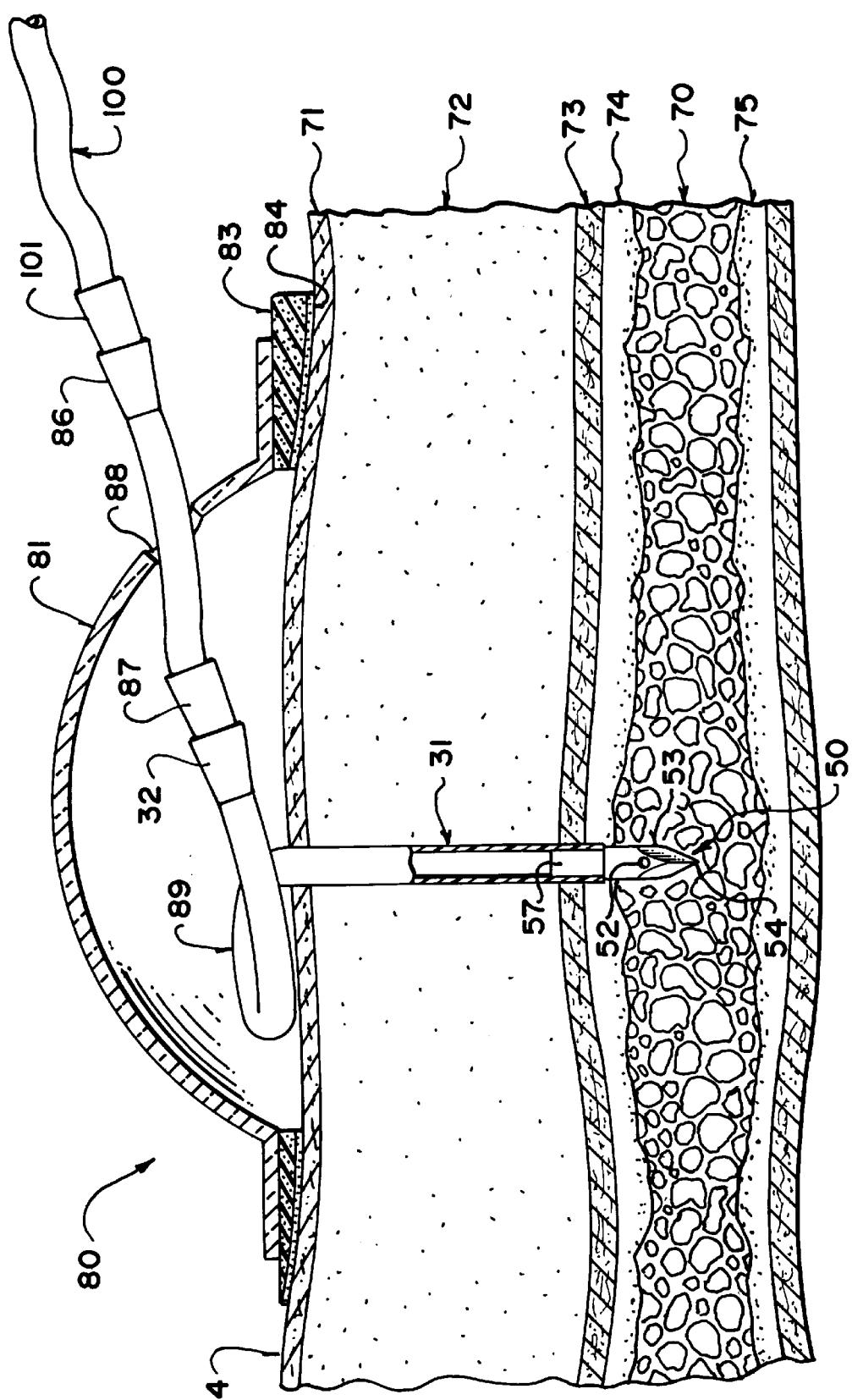
FIG. 11 represents a side partial section view of the protector, fluid transmitting connector tube, infusion tube and bone penetration means in place in a patient, without significant displacement of the overlying skin and tissue.
Figure 12:
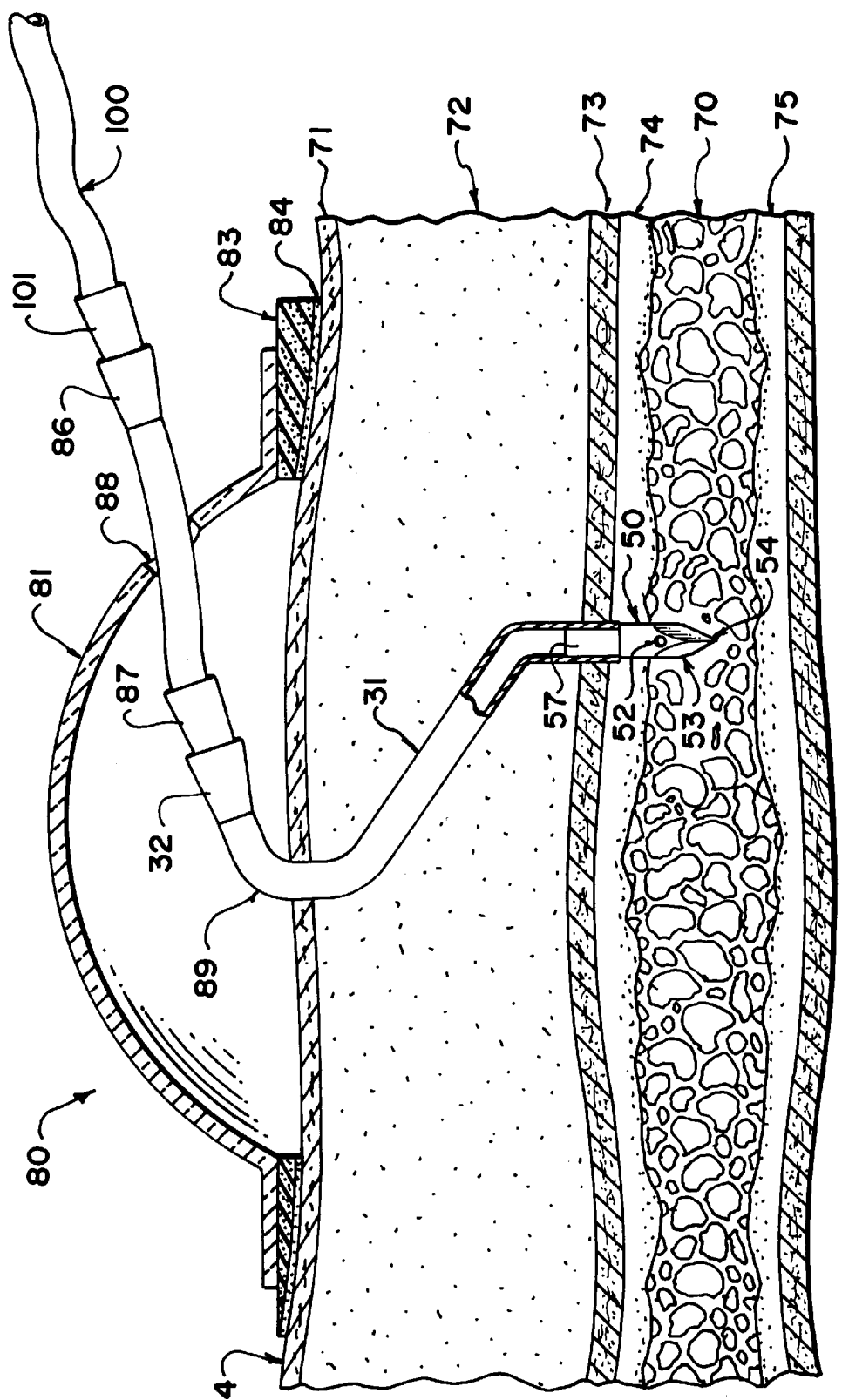
FIG. 12 represents a side partial section view of the protector, fluid transmitting connector tube, infusion tube and bone penetration means in place in a patient, where significant overlying skin and tissue movement has taken place after insertion.

FIG. 11 represents a side partial section view of the protector device and infusion tube and bone penetration means in place in a patient, without significant displacement of the overlying skin and tissue. For comparison, FIG. 12 represents a side partial section view of the infusion tube and bone penetration means in place in a patient, where significant overlying skin and tissue movement to the left has taken place after insertion. FIG. 11 with 12 show clearly that immunity of the bone penetration means 50 and infusion tube 30 from skin and tissue 71, 72 movement is achieved by positioning the bone penetration means 50 subcutaneously, and by providing slack 89 and a highly flexible tube 31 which can absorb movement. The bone penetration means 50 is sufficiently short and of low profile, and is so placed, that it lies subcutaneously entirely below the patient's skin 71 and below much of the subcutaneous tissue 72. In conjunction with the flexibility of the tubing 31, and the slack 89 associated with it, large movements can take place in the skin and tissue overlying the infusion site, without those movements disturbing the bone penetration means 50 embedded in the bone 74 and causing leakage or inadvertent removal of the bone penetration means 50.

Immunity of the system to large external forces is further achieved by providing a protector 80. No previous intraosseous infusion (101) devices have been provided with a protector system. In all previous devices, a part of the infusion device protrudes above the skin and that part is rigidly attached to the part of the intraosseous device that lies in the bone. Thus, in all prior art devices, forces that were applied to the part of the device protruding above the skin were transmitted to the part of the device in the bone and could thus act to loosen or jar the device in the bone, thereby resulting in unwanted leakage, or inadvertent removal.

In the subject invention, immunity to forces applied to the intravenous (IV) line that is connected to the infusion system is provided through the use of a protector 80 that transmits any lateral or longitudinal pulling force from the IV line to the skin 71, and not to the bone penetration means 50. These forces may arise in any number of ways, for example, from a person tripping on the line, or having the line caught during transport.

Reference to FIG. 11 will show that relief of strain on the bone penetration means 50 is achieved by fixing the end of the IV line 100 to a fluid transmitting connector 82 which is attached to the protector shell 81. Pulling forces applied along the IV line 100 are then transmitted to this fluid transmitting connector 82 and diverted through the shell 81, foam 83 and adhesive 84 to the patient's skin 71, rather than being transmitted through the fluid transmitting connector 82 to the distal end of the infusion tube 32.

This diversion of tension forces away from the bone penetration means 50 can be achieved in a number of ways. In the embodiment illustrated in FIGS. 9, 10, 11 and 12, the fluid transmitting connector 82 is a flexible tube that passes through a hole 88 in the protector shell 81. The hole 88 in the shell 81 is smaller than the fitting 87 that mates with the connection fitting means 32 on the infusion tube 31. When pulling forces are transmitted from the IV line 100 to the fitting 86, the tubing comprising fluid transmitting connector 82 moves through the hole 88 until the fitting 87 abuts the inside of the shell 81, and the fluid transmitting connector tubing 82 stops moving. When this occurs, the applied force is transmitted to the protector shell 81.

It will be appreciated that the fluid transmitting connector 82 can have many forms. The fluid transmitting connector 82 can include a flexible tube, or a rigid tube, or portions of each. The fluid transmitting connector 82 can traverse the hard shell 81, or the foam layer 83. The fluid transmitting connector 82 can pass through the hard shell 81 and have a abutment feature that comes up against the shell 81 when the protector system is in effect as described in this embodiment. Alternatively, the fluid transmitting connector 82 can be attached rigidly to the hard shell 81 so that it moves in neither direction.

The forces applied through the IV line 100, as well as other forces applied directly to the shell 81 and to surrounding skin and tissue can cause the shell 81 and underlying skin 71 to move with respect to the bone 74 in which the infusion tube 30 and bone penetration means 50 are fixed. Sufficient slack 89 in the flexible tubing 31 between the two ends of the infusion tube allow movement of the shell 81 and underlying skin 71 to occur without disturbing the bone penetration means 50. Thus the bone penetration means 50 attached to the proximal end of the tubing 31 remains protected from movement of the distal end of the tubing 31 and from external forces that are applied through the IV line 100, and the protector 81. The bone penetration means 50 is protected both by use of the protector 81 that diverts applied forces to the skin 71, and also by the presence of slack 89 in the infusion tube 30 which allows movement of the distal end 32 of the tube 31 without effect on bone penetration means 50.

The hard protector shell 81 also serves to protect the tubing 31 from forces that may be applied directly over the tubing 31. These forces could come from paramedic hands or medical equipment including a cervical spine collar. The hard shell 81 preserves the slack 89 in the tubing 31 by providing a space between the shell 81 and skin 71 in which the overall infusion tube 30 can freely move.

Immunity to extraordinarily large forces acting on the IV line 100 is also achieved by providing a slip-fit connection 101 between the IV line 100 and the protector fitting 86. The IV line conventionally has a male Luer fitting 101. The protector 80 has a female Luer fitting 86 that connects to the male Luer 101 on the IV line 100. Excessively large forces applied to the IV line will cause this connection to come apart. This break, which will only occur under extraordinarily abusive conditions, will be obvious to the user. The connection that comes apart acts as a safety mechanism to prevent extraordinarily large forces from being applied to the protector 80, the foam layer 83 and the skin bond 84, thus protecting the protector means 80 from accidental detachment from the skin 71, and withdrawal of the bone penetration means 50 in the bone 74.

FIG. 12 represents a side partial section view of the protector, fluid transmitting connector tube, infusion tube and bone penetration means in place in a patient, where significant overlying skin and tissue movement to the left has taken place after insertion.

In one embodiment, the use of sharp needles forming the bone stop means can be avoided for safety reasons. This is accomplished by a sliding skin port that pierces the skin, and comes to a stop a preset distance below the surface of the skin. The sliding skin port includes a hollow hypodermic type needle tip with a lumen, a skin stop that makes contact with the surface of the skin when the needle tip has advanced completely through the skin, and a slider that can move on the bone stop protrusion or rod. The sliding skin port can slidably move on the bone stop rod, which is blunt at its proximal end, and allows the bone stop protrusion or rod to be advanced through the hole in the slider and needle tip lumen as the blunt bone stop is advanced through the skin and overlying tissue.

FIG. 13 depicts another embodiment of the invention, namely, a side view of an applicator and infusion tube with two sliding skin port devices 44 slidably fitted over two separate sets of bone stop rod clusters 20. The purpose of the two sliding skin ports 40 is to enable blunt end bone stop rods 56 to be used in place of sharp end bone stop 56 needles. Rods with blunt ends are safer for handling by an administrator and have high resistance to penetrating bone. When used, the skin ports 44 fit over the proximal ends of rod clusters 20.

The manner in which the sliding bone stop functions is illustrated in sequence in FIGS. 15 and 16. FIG. 14 depicts an enlarged isometric view of a sliding skin port 40 on a blunt end bone stop protrusion rod 20. Specifically, FIG. 14 demonstrates in enlarged view how a single sliding skin port 40 slidably fits over a single bone stop protrusion rod 20. It will be understood that while FIGS. 14, 15 and 16 illustrate single ports 40 and single rods 20, there are corresponding sliding skin ports 40 for each protrusion rod 20 as illustrated broadly in FIG. 13.

FIG. 15 depicts a side partial section view of a bone stop rod 20 and a sliding skin port 40, mounted on the proximal end of rod 20 as skin port 40 begins to cut through skin 71. Specifically, FIG. 15 depicts a side partial section view of the skin port 40 and bone shaft 20, with sharp point 41 and slider skin stop 42, when a downward force has begun to be applied. The sharp point 41 takes the place of a sharp end needle and enables the rod 20 to penetrate the skin 71. FIG. 16 shows the subsequent position of the sliding skin port 40 and bone stop rod 20 after a downward force has pushed the blunt proximal end bone rod 20 through the skin stop slider 42 of the sliding skin port 40. The proximal side 43 (see FIG. 14) of the skin stop slider 42 has made contact with the skin 71, and the proximal blunt end of the bone stop rod 20 has penetrated the subcutaneous tissue and made contact with the periosteum 73.

As seen in FIG. 16, the bone stop protrusion rod 20 has moved partway through the hollow sliding skin port 40 as downward force has been applied to push the proximal blunt end of the bone stop rod 20 to contact the surface of the cortical bone 74 or periosteum 73. The hollow sharp tip 41 is adapted for cutting through the skin 71. The skin stop slider 42 is also hollow and slides up or down on the rod 20. The bottom surface of the slider 42 is a skin-stop 43 and prevents the sharp tip 41 from continuing down through the skin and overlying tissue 72 beyond a depth set by the relative position of the point of the sharp point 41 and the bottom surface 43 of the skin stop slider 42.

FIG. 17 depicts a bottom view of a sliding skin port with five sharp hollow points for fitting on one set of five rods of a rod cluster 20, as illustrated in FIG. 13. A corresponding sliding skin port fits over the other set of five rods. It is obvious that the sliding skin port 40 could contain a multiplicity of sharp tips 41 and sliding-fit holes to accommodate a multiplicity of bone stop rods 20 or protrusions. For example, in the embodiment illustrated in FIG. 17, each set of the rod cluster, which contains five rods 20, can be fitted with one sliding skin port 44, that accommodates the five bone stop rods. A symmetrical sliding skin port 44 fits over the other five rods of the facing set of rod clusters seen in FIG. 13.

It will be recognized that the bone stop 56 can have any of a number of shapes and sizes. Requirements for the bone stop are that it: (1) resist being pushed through the distal cortical bone 74 with a force much greater than that required to force the sharp tip of the stylet 12 and/or the sharp tip of the bone penetration means 50 through the cortical bone 74; (2) make positive resistive contact with the outer surface of the periosteum 73 or cortical bone 74 in a way that can be clearly felt by the administrator 6; (3) and when it is in contact with the cortical bone 74 or periosteum 73 it ensures the fluid delivery ports 52 of the bone penetration means 50 are at the correct depth in the marrow space 70 regardless of the thickness of overlying skin 71 and tissue 72.

Similarly, it will be understood that the subcutaneous bone penetration means 50 can have any of a number of shapes and sizes. Requirements for the subcutaneous penetration means include that it: (1) after correct placement, has a low profile and resides subcutaneously below the skin 71 and much of the tissue 72 overlying the infusion site; (2) be attachable to a flexible tubing 31; (3) be able to deliver fluid to the marrow space 70 into which it protrudes; (4) be sufficiently well anchored that it is undisturbed by the small forces that may be transmitted to it; and (5) that it either be able to be removed, or be absorbed into the patient's body, or be sufficiently biocompatible that it may be left permanently in place in the patient, without rejection by the patient.

Likewise, it will be recognized that the fluid transmitting connector 82 can have many forms. Requirements for the fluid transmitting connector 82 are that it: (1) include two fitting means 86, 87 suitable for linking the infusion/aspiration tube and the sources of fluid to be infused, or sources of suction for aspiration; (2) allow passage of fluid being infused or aspirated; (3) provide a stop to movement and forces arising from the connecting lines or devices that comprise the sources of fluid to be infused, or sources of suction for aspiration, thereby protecting the infusion/aspiration tube from these motions and forces; (4) provide the infusion/aspiration tube with sufficient slack to accommodate skin motion when the protector 80 has been attached to the patient's skin; and (5) be easy to install on the infusion/aspiration tube without subjecting the infusion/aspiration tube to excessive forces.

The hard shell 81 and foam layer 83 can also have any number of shapes and sizes. Requirements for the hard shell are that it: (1) attach to the patient's skin and accommodate the topographical variation in anatomy around the infusion site; (2) provide for sufficient slack 89 in the infusion/aspiration tube when it is placed on the skin, and when the fitting 87 has been attached to the infusion/aspiration tube 30; (3) be sufficiently strong to maintain the required slack and protect the infusion/aspiration tube from external forces applied directly to the shell; and (4) allow the care provider to see the infusion site.

Similarly, it will be understood that the handle 11 of the applicator 10 can have any of a number of shapes and sizes, the only significant requirement being that it should be ergonomically designed so that the operator (administrator) be able to conveniently grasp it and apply the required bone penetration means installation force. A suitable surface roughened or scored texture (not shown) or other grasp enhancing irregularities in the handle's outer surface will facilitate such grasping. The handle 11 may be made from any suitable material having the requisite strength to withstand normal handling.

Method of Installation and Use of Applicator and Infusion Tube

The preferred method of installing and using the intraosseous infusion apparatus is as follows. First the target infusion site on the patient is located and cleaned. When the target bone for the device is the sternum (as shown in FIG. 1), the intended infusion site is located by simply palpating the deep notch at the top of the sternum, and measuring one finger width down from it on the centre line of the sternum, thus easily and accurately targeting the desired location on the manubrium.

The complete apparatus 1 (that is the applicator 10 and the infusion/aspiration tube 30 fitted together) is then positioned with the sharp tip 16 of the stylet 12 and/or sharp tip of the bone penetration means 54 over the skin at the intended infusion site. The proximal ends 18 of the applicator 10 are squeezed together so that they support the stylet 12 and tube 30. The apparatus is then advanced manually by the administrator until the reference plane 58 of bone stop 56 makes contact with the cortical bone 74 or periosteum 73 (see FIG. 8), whereupon the apparatus cannot be further advanced using moderate manual force. The bone stop 56 will thus ensure that the fluid delivery ports 52 of the insertion/aspiration tube are placed at precisely the correct depth in the marrow space 70, and that no overpenetration occurs. There is thus no dependency on the thickness of the overlying skin 71 and tissue 72.

After insertion of the bone penetration means 50 into the cortical bone 74 is completed to the correct marrow depth as determined by the bone stop 56, the applicator 10 is withdrawn. The infusion tube fitting 32 may then be connected to a source of fluid or vacuum to allow liquid infusion into the marrow or marrow aspiration to take place.

Alternatively, when the protector 80 system is used, the infusion tube fitting 32 may be attached to the proximal end 87 of the fluid transmitting connector 82 in the protector 80. The protector 80 is then placed on the skin 71 at a location such that all of the tube 31 and fitting 32 which is outside the patient is accommodated within the hard shell 81 and is free to move within it. Thus any movement of the shell 81 and underlying skin, or of the skin 71 or tissue 72 relative to the bone penetration means 50 and cortical bone 74 will be taken up as a variation in the amount of slack 89 in the infusion tube 31 (see FIG. 11). After the protector 80 has been attached to the patient's skin 71, the distal end 86 of its fluid transmitting connector 82 may be connected to a source of fluid or vacuum to allow liquid infusion or aspiration to take place.

Once the infusion tube 30 or the protector 80 has been properly connected to a source of infusion fluid, liquid can be infused into the bone marrow 70 through the infusion tube 30 (and optionally, the fluid transmitting connector 82) and the fluid delivery ports 52 in the penetration means's proximal end 53. The liquid is delivered to the tube via a connection fitting 32 located at the distal end of the infusion tube 31. The fitting may be adapted for connection to a protector system or to any conventional infusion device (not shown in the drawings), such as an autoinjection canister, gravity feed bag, or syringe. The liquid being delivered can be a resuscitation fluid or any other standard vascular delivery drug. Alternatively, connection may be made to a source of vacuum for marrow aspiration.

Those persons skilled in the art will appreciate that the method for use of the invention is simple, quick and reliable and comprises a short series of simple steps: (1) identify the correct location; (2) if the target bone is the manubrium use the location method of finding the sternal notch and measuring one finger width down the midline; (3) place the bone penetration means tip of the apparatus over the skin at the correct location; (4) advance the apparatus including the applicator with moderate force until the bone stop is felt to make contact with the periosteum or the outer surface of the outer cortical bone; (5) withdraw the applicator; (6) optionally connect the protector means to the infusion tube and patient; and (7) attach the system to the appropriate source of fluids or suction. Thus the apparatus can be used to obtain fast, safe and reliable access to the circulatory system of a patient, by a method which calls for minimal skills and training, and in particular by a method that involves less skill and training than the method of peripheral intravenous access.

It will be recognized that the various embodiments discussed and illustrated above can be used alternatively to aspirate marrow from the patient's bone, rather than infuse a liquid into it. No significant alterations need be made to the embodiments, other than to adapt the distal end of the infusion tube 31 (now an aspiration tube) or fitting 86 on the protector for connection to a suitable aspirator.

It should be appreciated from the foregoing description that the present invention provides an improved apparatus and related method for infusing liquids into, and/or aspirating marrow from the marrow space of a patient's bone. The apparatus enables the user to achieve fast, safe and reliable vascular access in the field, battlefield or first-response emergency environment, with a low level of user skill, and regardless of the thickness of skin and tissue over the chosen infusion/aspiration site. The apparatus ensures the access device will remain in place throughout other emergency procedures and severe environmental conditions.

Although the invention has been described in detail with reference to the presently preferred embodiments, those of ordinary skill in the art will appreciate that various modifications can be made without departing from the invention. Accordingly, the invention is defined only by the following claims.

What is claimed is:

1. A bone-installed apparatus for intraosseous fluid infusion or aspiration of bone marrow of a patient, comprising a fluid conduit having a distal end and a proximal end, the distal end of the fluid conduit being movable relative to the proximal end, the proximal end adapted to be installed in the bone of the patient.

2. An apparatus as claimed in claim 1 including a bone penetration means with a proximal end, and a distal end connected to the fluid conduit.

3. An apparatus as claimed in claim 1 wherein a proximal part of the fluid conduit is a bone penetration means and the bone penetration means has a lumen fluid transmission means therein extending from a proximal end to a distal end.

4. An apparatus as claimed in claim 3 wherein a part of the fluid conduit is a flexible tubing which is connected to the distal end of the lumen fluid transmission means of the bone penetration means.

5. An apparatus as claimed in claim 2 including an applicator means which detachably engages the bone penetration means and enables an administrator to cause the proximal end of the bone penetration means to penetrate part of a bone and part of underlying bone marrow of the patient.

6. An apparatus as claimed in claim 3 wherein the bone penetration means has a port in its proximal end connected to the lumen.

7. An apparatus as claimed in claim 2 wherein the proximal end of the bone penetration means is sharp.

8. An apparatus as claimed in claim 5 wherein a part of the fluid conduit is a flexible tubing.

9. An apparatus as claimed in claim 2 wherein the bone penetration means has a low profile and when installed subcutaneously in the patient, the distal end of the bone penetration means does not protrude above the skin of the patient.

10. An apparatus as claimed in claim 5 wherein the applicator means is a handle and an associated rigid stylet, which penetrates the interior of the fluid conduit, contacts the bone penetration means, and enables an administrator to cause the proximal end of the bone penetration means to penetrate through surface bone and into the underlying bone marrow of the patient.

11. An apparatus as claimed in claim 2 wherein the length of the fluid conduit is sufficient to permit a surplus of fluid conduit between the proximal end and the distal end so that the distal end of the fluid conduit can be moved without disturbing a proximal end of the fluid conduit which is connected to the distal end of the bone penetration means.

12. A bone-installed apparatus for intraosseous fluid infusion or aspiration of bone marrow of a patient, comprising:

(a) a fluid conduit having a distal end and a proximal end; and (b a bone stop means, a proximal side of the bone stop means adapted to impinge against a surface of the bone when the proximal end of the fluid conduit is located in underlying bone marrow.

13. An apparatus as claimed in claim 12 including a bone penetration means with a proximal end and a distal end connected to the fluid conduit.

14. An apparatus as claimed in claim 13 including an applicator means which detachably engages the bone penetration means and enables an administrator to cause the proximal end of the bone penetration means to penetrate part of a bone and part of underlying bone marrow of the patient.

15. An apparatus as claimed in claim 14 wherein the bone stop means is located on a proximal end of the applicator means.

16. An apparatus as claimed in claim 14 wherein the bone stop means comprises a plurality of rods which protrude from a proximal end of the applicator means.

17. An apparatus as claimed in claim 16 wherein the rods encircle at least part of the distal end of the bone penetration means.

18. An apparatus as claimed in claim 14 wherein the applicator means is hollow, elongated and open at one end, a stylet having a distal end and a proximal end is located longitudinally within the hollow of the applicator means, the proximal end of the stylet protruding from the hollow through the open end, and the bone stop means is located on a proximal end of the applicator means adjacent to the open end.

19. An apparatus as claimed in claim 18 wherein the applicator means is bifurcated and open on each side to provide a first proximal part and a second proximal part, the stylet being accessible through the openings on each side between the first proximal part and the second proximal part, and from the open end of the hollow applicator means, the bone stop means comprising a pair of clusters of longitudinally extending rods, the first of the pair of rod clusters being located at the proximal end of the first proximal part and the second of the pair of rod clusters being located at the proximal end of the second proximal part.

20. An apparatus as claimed in claim 19 wherein proximal tips of the first proximal part and proximal tips of the second proximal part can be moved together to support lateral sides of the stylet.

21. An apparatus as claimed in claim 15 including a protective covering which removably fits over the bone stop means.

22. An apparatus as claimed in claim 16 including a sliding stop means which slidably fits on the plurality of rods, the sliding stop means having sharp, hollow proximal points which correspond in number and location with the number of rods, the hollow proximal points enabling the respective plurality of rods to slide through the corresponding hollow proximal points.

23. A low profile bone penetration apparatus for subcutaneous intraosseous fluid infusion into or aspiration of bone marrow of a patient comprising:

(a) a sharp proximal end for penetrating surface bone and a portion of underlying bone marrow of the patient;

(b) at least one port located on a side of the apparatus adjacent to the sharp proximal end;

(c) a surface for impinging against a bearing surface of a detachable applicator; and (d) a hollow distal end connected internally with the port by a lumen which enables a fluid conveyance means to be detachably connected to the hollow distal end, the length between the hollow distal end and a reference point distal to the proximal end being less than the depth of tissue and skin overlying the bone of the patient so that the bone penetration apparatus adapted to impinge subcutaneously in the patient.

24. An apparatus as claimed in claim 23 wherein the port is located at the proximal end and connects with the lumen.

25. An apparatus as claimed in claim 23 wherein a plurality of ports is located in the sides of the penetration apparatus adjacent to the sharp proximal end and at a distance from the proximal end which is adjacent to bone marrow when the bone penetration apparatus resides subcutaneously in the patient, said side ports connecting with the lumen.

26. An apparatus comprising: (a) a bone penetration means with a proximal end and a distal end and lumen fluid transmission means therein extending from the proximal end to the distal end; (b) an applicator means which detachably engages the bone penetration means and enables an administrator to cause the proximal end of the bone penetration means to penetrate part of a bone and part of the underlying marrow of the patient; and (c) a fluid conveyance means which is connected to the lumen fluid transmission means at the distal end of the bone penetration means.

27. An apparatus comprising: (a) a bone penetration means with a proximal end and a distal end and lumen fluid transmission means therein extending from the proximal end to the distal end; (b) an applicator means which detachably engages the bone penetration means and enables an administrator to cause the proximal end of the bone penetration means to penetrate part of a bone and part of the underlying marrow of the patient; and (c) bone stop, means, a proximal side of the bone stop means adapted to impinge against the surface of the bone of the patient when the proximal end of the bone penetration means penetrates the surface bone and a part of the marrow of the patient.

\* \* \* \* \*